(12) United States Patent
Sakamoto et al.

(10) Patent No.: US 9,644,124 B2
(45) Date of Patent: May 9, 2017

(54) SILICON-CONTAINING COMPOUND HAVING ALKOXYSILYL-ETHYLENE GROUP AT ITS TERMINAL, ROOM TEMPERATURE-CURABLE ORGANOPOLYSILOXANE COMPOSITION, AND MOLDED PRODUCT OBTAINED BY CURING THE COMPOSITION

(71) Applicant: SHIN-ETSU CHEMICAL CO., LTD., Tokyo (JP)

(72) Inventors: Takafumi Sakamoto, Annaka (JP); Takahiro Yamaguchi, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/649,030

(22) PCT Filed: Dec. 10, 2013

(86) PCT No.: PCT/JP2013/007247
§ 371 (c)(1),
(2) Date: Jun. 2, 2015

(87) PCT Pub. No.: WO2014/097574
PCT Pub. Date: Jun. 26, 2014

(65) Prior Publication Data
US 2015/0315438 A1    Nov. 5, 2015

(30) Foreign Application Priority Data

Dec. 20, 2012  (JP) .................................. 2012-277863
Apr. 12, 2013  (JP) .................................. 2013-084075
Apr. 12, 2013  (JP) .................................. 2013-084149

(51) Int. Cl.
*C08G 77/20* (2006.01)
*C09J 183/06* (2006.01)
(Continued)

(52) U.S. Cl.
CPC .......... *C09J 183/06* (2013.01); *C07F 7/0849* (2013.01); *C07F 7/1836* (2013.01);
(Continued)

(58) Field of Classification Search
None
See application file for complete search history.

(56) References Cited

U.S. PATENT DOCUMENTS 3,595,733 A    7/1971  Ching et al.
5,489,662 A *  2/1996  Wakamatsu ........... C08G 77/60
                                                    528/14
(Continued)

FOREIGN PATENT DOCUMENTS

CN    102464671 A    5/2012
JP    S3927643 B    2/1964
(Continued)

OTHER PUBLICATIONS

Mar. 4, 2014 International Search Report issued in International Application No. PCT/JP2013/007247.
(Continued)

*Primary Examiner* — Robert S Loewe
(74) *Attorney, Agent, or Firm* — Oliff PLC

(57) ABSTRACT

A silicon-containing compound having an alkoxysilyl-ethylene group at its terminal including at least one silyl-ethylene bond represented by the following structural formula (a) in one molecule, and according to this compound, a novel base polymer used in a room temperature-curable polyorganosiloxane composition capable of providing a cured product that is particularly excellent in rapid curability, storage stability and durability can be provided.

(Continued)

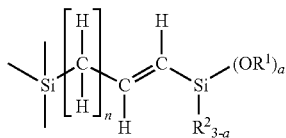

(a)

19 Claims, 8 Drawing Sheets

(51) Int. Cl.

| | |
|---|---|
| C08F 130/08 | (2006.01) |
| C09D 183/06 | (2006.01) |
| C08K 5/5425 | (2006.01) |
| C08G 77/50 | (2006.01) |
| C08L 83/06 | (2006.01) |
| C07F 7/08 | (2006.01) |
| C07F 7/18 | (2006.01) |
| C08G 77/38 | (2006.01) |
| C08L 83/04 | (2006.01) |

(52) U.S. Cl.
CPC ............ *C08F 130/08* (2013.01); *C08G 77/20* (2013.01); *C08G 77/38* (2013.01); *C08G 77/50* (2013.01); *C08K 5/5425* (2013.01); *C08L 83/04* (2013.01); *C08L 83/06* (2013.01); *C09D 183/06* (2013.01)

(56) References Cited

U.S. PATENT DOCUMENTS

| | | |
|---|---|---|
| 2005/0194619 A1 | 9/2005 | Edelstein et al. |
| 2006/0165891 A1 | 7/2006 | Edelstein et al. |
| 2009/0181178 A1 | 7/2009 | Edelstein et al. |
| 2011/0101489 A1 | 5/2011 | Edelstein et al. |
| 2011/0257324 A1 | 10/2011 | Ziche et al. |
| 2012/0020700 A1 | 1/2012 | Yamada et al. |
| 2012/0123143 A1 | 5/2012 | Popp et al. |

FOREIGN PATENT DOCUMENTS

| | | |
|---|---|---|
| JP | S506456 B1 | 3/1975 |
| JP | S5543119 A | 3/1980 |
| JP | S56122390 A | 9/1981 |
| JP | H4283589 A | 10/1992 |
| JP | H739547 B2 | 5/1995 |
| JP | H7331076 A | 12/1995 |
| JP | 2006216541 A | 8/2006 |
| JP | 201232804 A | 2/2012 |
| JP | 2012511607 A | 5/2012 |
| WO | 2012/001881 A1 | 1/2012 |
| WO | 2012/018598 A1 | 2/2012 |
| WO | 2013/081794 A1 | 6/2013 |

OTHER PUBLICATIONS

Jun. 23, 2015 International Preliminary Report on Patentability issued in International Application No. PCT/JP2013/007247.

Jun. 7, 2016 Office Action issued in Japanese Application No. 2014-552911.

Pietraszuk et al., "Cross-metathesis of vinylsilanes with olefins in the presence of Grubbs' catalyst," Tetrahedron Letters, 42 (2001) 1175-1178.

Jun. 20, 2016 extended European Search Report issued in Application No. 13865466.0.

Dec. 14, 2016 Office Action issued in Chinese Patent Application No. 201380067447.4.

\* cited by examiner

SILICON-CONTAINING COMPOUND HAVING ALKOXYSILYL-ETHYLENE GROUP AT ITS TERMINAL, ROOM TEMPERATURE-CURABLE ORGANOPOLYSILOXANE COMPOSITION, AND MOLDED PRODUCT OBTAINED BY CURING THE COMPOSITION

TECHNICAL FIELD

The present invention relates to a silicon-containing compound having an alkoxysilyl-ethylene group at its terminal, a room temperature-curable organopolysiloxane composition, and a molded product obtained by curing the composition.

BACKGROUND ART

A room temperature curable composition which cures an elastomer state at room temperature by a condensation and crosslinking reaction from contact with the moisture in the air, particularly a room temperature-curable organopolysiloxane composition has conventionally been known in various types of materials, and above all, a material of the type which cures by discharging alcohol is preferably used for sealing, adhesion or coating of an electric and electronic devices, etc., due to its characteristics that there is no unpleasant smell and it does not corrode metals.

As representative example of such a type, a room temperature-curable organopolysiloxane composition comprising a polyorganosiloxane the terminal of which has been blocked by a hydroxyl group, an alkoxysilane and an organotitanium compound; a room temperature-curable organopolysiloxane composition comprising a polyorganosiloxane the terminal of which has been blocked by an alkoxysilyl, an alkoxysilane and an alkoxytitanium; a room temperature-curable organopolysiloxane composition comprising a linear polyorganosiloxane the terminal of which has been blocked by an alkoxysilyl group containing a silethylene group, an alkoxysilane and an alkoxytitanium; and a room temperature-curable organopolysiloxane composition comprising a polyorganosiloxane the terminal of which has been blocked by a hydroxyl group or a polyorganosiloxane the terminal of which has been blocked by an alkoxy group and an alkoxy-α-silyl ester compound have been disclosed (Patent Literatures 1 to 4).

These compositions are advantageously employed in view of a certain level of storage stability, water resistance, and humidity resistance. However, these problems have not been completely solved yet. Further, they were insufficient with regard to rapid curability.

As described above, a polymer having a reactive alkoxysilyl group has conventionally been known. The terminal group of this polymer has previously been blocked by an alkoxysilyl group, so that curability of the polymer difficultly change (lower) with a lapse of time, and a composition that is excellent in storage stability can be obtained. Also, workability (viscosity and thixotropic property) thereof can be optionally adjustable, and it reacts with a moisture in the air to form an elastomer by crosslinking, whereby excellent characteristics (hardness, tensile strength and elongation at break) can be also obtained.

However, a dealcoholization type of room temperature-curable organopolysiloxane composition comprising an organosiloxane polymer having such a reactive alkoxysilyl group at its terminal as a main agent (a base polymer) was insufficient in curability as compared to the other conventionally known curing types such as a deoximation type, a deacetylation type, a deacetone type, etc., since reactivity with a moisture in the air is low.

In response thereto, researches focused on a functional group (a bonding group) adjacent to the reactive alkoxy group have been promoted, and it has been reported that an α-alkoxysilylmethyl terminal group has particularly high reactivity with a moisture in the air (Patent Literature 5). However, curability thereof is yet insufficient, and there are defects that the adjacent functional group (a bonding group) exerts bad effect to durability, and a restoring force of the cured product is low.

CITATION LIST

Patent Literature

PATENT LITERATURE 1: JP Sho.39-27643B
PATENT LITERATURE 2: JP Sho.55-43119A
PATENT LITERATURE 3: JP Hei.7-39547B
PATENT LITERATURE 4: JP Hei.7-331076A
PATENT LITERATURE 5: JP 2012-511607A

SUMMARY OF THE INVENTION

Technical Problem

The present invention has been done in view of the circumstances, and an object thereof is to provide a room temperature-curable polyorganosiloxane composition capable of providing a cured product that is excellent in rapid curability, storage stability and durability, and a novel base polymer used in the composition or a curing agent (a crosslinking agent) thereof.

Solution to Problem

To solve the problems as mentioned above, the present invention provides a silicon-containing compound having an alkoxysilyl-ethylene group at its terminal (for example, an organosilane compound and an organosiloxane compound) which comprises at least one silyl-ethylene bond represented by the following structural formula (a) in one molecule, and a novel room temperature curable composition by using the silicon-containing compound as a base polymer or a curing agent (a crosslinking agent),

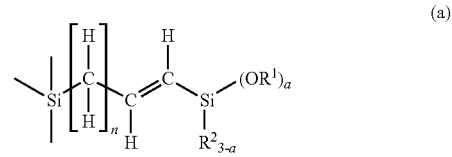

(a)

wherein $R^1$ represents a monovalent hydrocarbon group having 1 to 20 carbon atoms which may have a substituent, and the hydrocarbon group having 3 or more carbon atoms may be a cycloalkyl group which is cyclic; $R^2$ represents a hydrogen atom, or a monovalent hydrocarbon group having 1 to 20 carbon atoms which may have a substituent; "a" represents an integer of 1 to 3; and "n" represents an integer of 0 to 10.

When the silicon-containing compound having an alkoxysilyl-ethylene group at its terminal is used as a base polymer or a curing agent (a crosslinking agent), a room temperature curable composition capable of providing a cured product that is excellent in rapid curability, storage stability and durability can be obtained.

Also, the formula (a) preferably contains at least one organosiloxy group (n=0) having a silyl-ethylene structure in one molecule, or at least one organosiloxy group (n≥1) having an alkyl group substituted by the silyl-ethylene structure in one molecule each represented by the following structural formula (1)

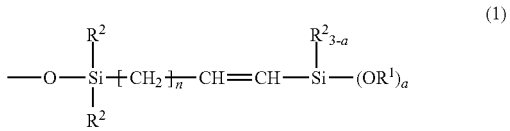

(1)

wherein $R^1$ and $R^2$, "a", and "n" are the same as before.

If the silicon-containing compound having an alkoxysilyl-ethylene group at its terminal is used as, for example, a base polymer (linear diorganopolysiloxane) or a crosslinking agent (organosilane and a partial hydrolysis condensate thereof) of a room temperature-curable organopolysiloxane composition, the room temperature-curable organopolysiloxane composition can provide a cured product that is particularly excellent in rapid curability, storage stability and durability.

Also, the polyorganosiloxane compound having an alkoxysilyl-ethylene group at its terminal is preferably linear diorganopolysiloxane both terminals of a molecular chain of which have been blocked by organosiloxy groups having an alkoxysilyl-ethylene structure represented by the following structural formula (2),

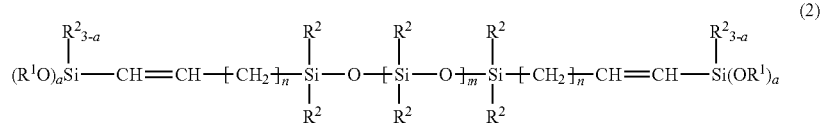

(2)

wherein $R^1$ and $R^2$, "a" and "n" are the same as before; and "m" represents an integer of 0 to 2,000.

The polyorganosiloxane compound having an alkoxysilyl-ethylene group at its terminals can provide an organopolysiloxane cured product (silicone rubber) that is more excellent in rapid curability, storage stability and durability.

In addition, the present invention provides a room temperature-curable organopolysiloxane composition comprising:

(A) a diorganopolysiloxane containing at least 2 silicon atoms to which a hydroxyl group and/or a hydrolyzable silyl group are bonded in one molecule: 100 parts by mass;
(B) the silicon-containing compound having an alkoxysilyl-ethylene group at its terminal: 0.1 to 30 parts by mass;
(C) a curing catalyst: 0.001 to 15 parts by mass;
(D) a silane and/or a partial hydrolysis condensate thereof other than the component (B): 0 to 30 parts by mass;
(E) a filler: 0 to 1,000 parts by mass; and
(F) an adhesion promoter: 0 to 30 parts by mass.

The room temperature-curable organopolysiloxane composition can provide a cured product (silicone rubber) that is particularly excellent in rapid curability, storage stability and durability.

Also, the room temperature-curable organopolysiloxane composition is preferably used as either of a coating agent, an adhesive and a sealing agent.

The room temperature-curable organopolysiloxane composition is useful as a coating agent, an adhesive or a sealing agent at positions where heat resistance, water resistance and humidity resistance are required.

Also, the present invention provides a molded product (a silicone rubber molded product) obtained by curing the room temperature-curable organopolysiloxane composition of the present invention.

The molded product can form a rubber-elastic cured product that is excellent in heat resistance, weather resistance, low temperature characteristics, and adhesiveness to the various kinds of substrate materials, particularly to a metal, by being rapidly cured.

Advantageous Effects of Invention

As described above, the novel silicon-containing compound (for example, an organosilane compound and an organosiloxane compound, etc.) of the present invention provides a cured product that is particularly excellent in rapid curability. Even after storage of, for example, 12 months, the compound is rapidly cured when exposed to the air and shows excellent physical properties. Additionally, a composition containing the novel silicon-containing compound as a base polymer or a curing agent (a crosslinking agent) is useful as an adhesive or sealing agent at positions where heat resistance, water resistance, and humidity resistance are required, and above all, it can effectively be used as building use required to have steam resistance and water resistance, and an adhesive on construction use for electric and electronic equipments.

DESCRIPTION OF EMBODIMENTS

Figure 1:
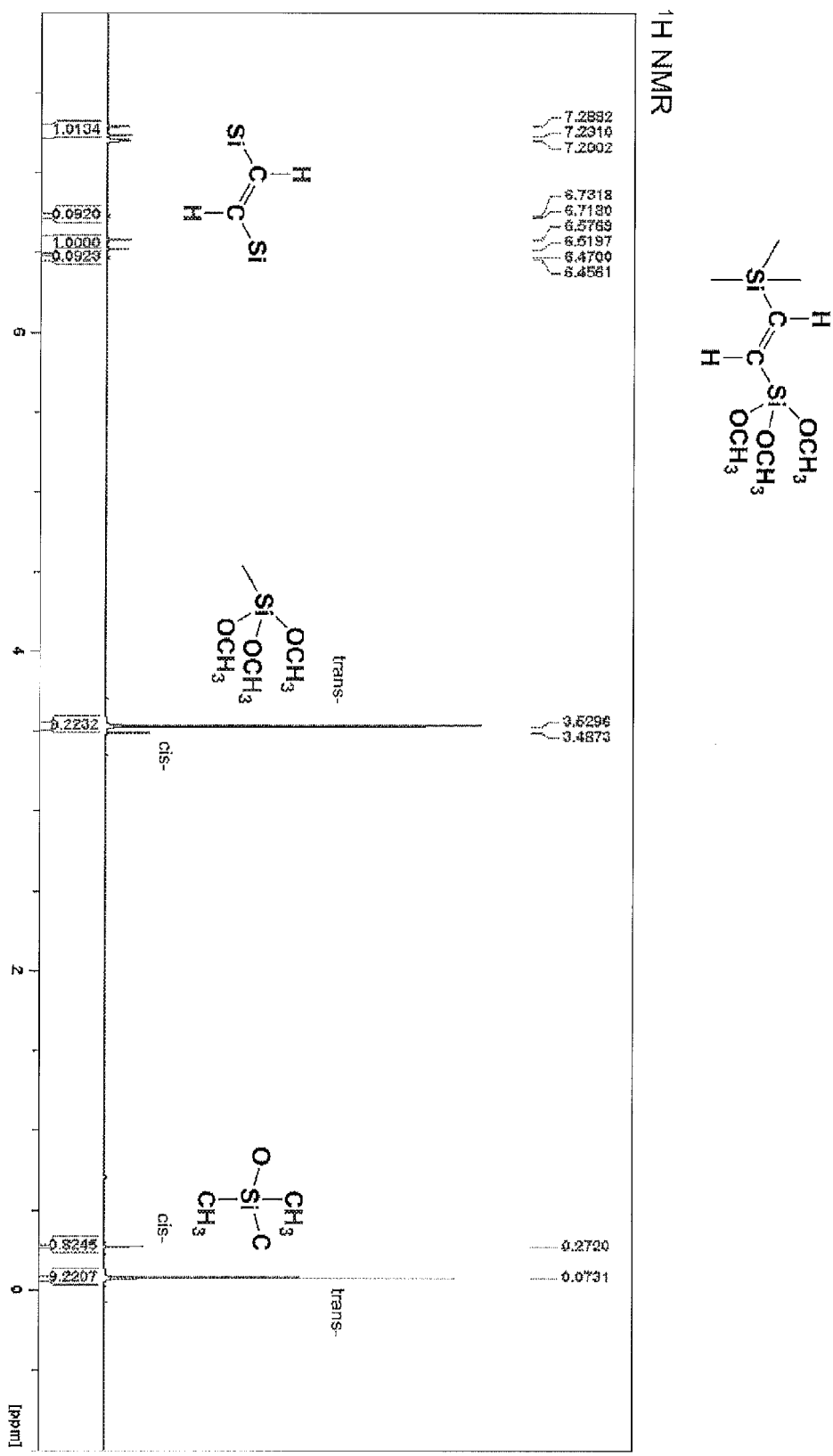
FIG. 1 shows a $^1$H-NMR-chart of a compound 1 obtained in a Synthesis Example 1 (a trimethoxysilyl-ethylene-substituted trimethylsilane)

As described above, development of a room temperature-curable organopolysiloxane composition and a novel base polymer or a curing agent (a crosslinking agent) used in the composition capable of providing a cured product that is particularly excellent in rapid curability, storage stability and durability has been desired.

Inventors of the present invention have carried out extended research and found that as long as a bonding group adjacent to an alkoxysilyl group is an ethylene hydrocarbon, a hydrolyzable property of an alkoxy group is significantly improved, and according to silicon compound having an alkoxysilyl-ethylene group at its terminal represented by the following structural formula (a), particularly the following structural formula (1), a room temperature curable composition which gives a cured product particularly excellent in rapid curability, and simultaneously having favorable storage stability and durability can be obtained. Based on that information, the present invention was accomplished.

Specifically, the novel silicon-containing compound of the present invention is an silicon-containing organic silicon compound having an alkoxysilyl-ethylene group at its terminal which comprises at least one organosilyl group having a silyl-ethylene bond represented by the following structural formula (a) in one molecule,

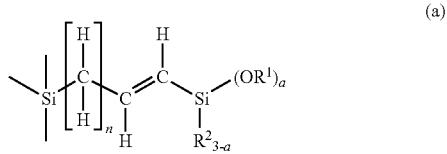

(a)

wherein $R^1$ represents a monovalent hydrocarbon group having 1 to 20 carbon atoms which may have a substituent, and those having 3 or more carbon atoms among the hydrocarbon groups may be a cycloalkyl group which is cyclic; $R^2$ represents a hydrogen atom, or a monovalent hydrocarbon group having 1 to 20 carbon atoms which may have a substituent; "a" represents an integer of 1 to 3; and "n" represents an integer of 0 to 10.

Also, the formula (a) preferably contains at least one organosiloxy group (n=0) having a silyl-ethylene bond represented by the following structural formula (1) in one molecule, or at least one organosiloxy group (n1) having an alkyl group substituted by the silyl-ethylene structure in one molecule,

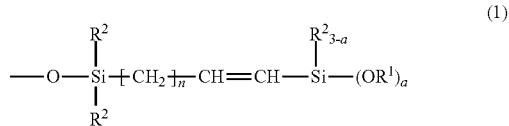

(1)

wherein $R^1$ and $R^2$, "a" and "n" are the same as before.

Also, the silicon-containing compound having an alkoxysilyl-ethylene group at its terminal is preferably linear diorganopolysiloxane both terminals of a molecular chain of which have been blocked by organosiloxy groups having an alkoxysilyl-ethylene structure represented by the following structural formula (2),

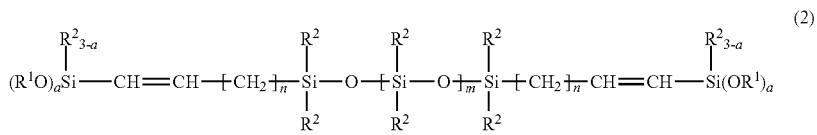

(2)

wherein $R^1$ and $R^2$, "a" and "n" are the same as before; and "m" represents an integer of 0 to 2,000.

The present invention will be described in detail.

<Silicon-Containing Compound Having Alkoxysilyl-Ethylene Group at its Terminal>

The silicon-containing compound having an alkoxysilyl-ethylene group at its terminal according to the present invention is an organic silicon compound such as an organosilane compound and an organosiloxane compound containing at least one silyl-ethylene bond in one molecule.

Herein, in the above structural formulae (a), (1) and (2), the substituted or unsubstituted monovalent hydrocarbon group of $R^1$ and $R^2$ having 1 to 20 carbon atoms, preferably having 1 to 10 carbon atoms, and more preferably having 1 to 6 carbon atoms may be exemplified by an alkyl group such as a methyl group, an ethyl group, a propyl group, an isopropyl group, a butyl group, an isobutyl group, a tert-butyl group, a pentyl group, a hexyl group, a heptyl group, an octyl group, a nonyl group, a decyl group, an octadecyl group, etc.; a cycloalkyl group such as a cyclopentyl group, a cyclohexyl group, etc.; and a group in which a part or all of hydrogen atoms of these groups is/are substituted by a halogen atom such as F, Cl, Br, etc. or a cyano group, or a lower alkoxy group such as a methoxy group, an ethoxy group, etc., for example, a 3-chloropropyl group, a 3,3,3-trifluoropropyl group, a 2-cyanoethyl group, a methoxyethoxy group, etc. Among these, a methyl group and an ethyl group are preferable, and a methyl group is particularly preferable.

Also, $R^2$ in the above structural formula (2) additionally may be exemplified by a hydrogen atom; an alkenyl group such as a vinyl group, an allyl group, a propenyl group, a butenyl group, a pentenyl group, a hexenyl group, etc.; an aryl group such as a phenyl group, a tolyl group, a xylyl group, an α-, β-naphthyl group, etc.; an aralkyl group such as a benzyl group, a 2-phenylethyl group, a 3-phenylpropyl group, etc.; and a group in which a part or all of hydrogen atoms of these groups is/are substituted by a halogen atom such as F, Cl, Br, etc., or a cyano group, etc.

Illustrative example of a hydrolyzable group at a terminal of a molecular chain (($OR^1$)$_a$ in the above structural formulae (a), (1), and (2)) includes an alkoxy group having 1 to 5 carbon atoms such as a methoxy group, an ethoxy group, a propoxy group, an isopropoxy group, a butoxy group, an isobutoxy group, a tert-butoxy group, etc.; an alkoxyalkoxy group having 1 to 5 carbon atoms such as a methoxyethoxy group, a methoxypropoxy group, an ethoxypropoxy group, etc. Among these, a methoxy group and an ethoxy group are particularly preferable.

Also, as described above, "n" represents an integer of 0 to 10, preferably 0 to 5, and more preferably 0 to 3; "m" represents an integer of 0 to 2,000, preferably 0 to 1600, more preferably 0 to 1,000, and much more preferably 0 to 500; and "a" represents an integer of 1 to 3.

If "n" is more than 10, the reactive property is reduced and it is technically disadvantageous. If "m" is less than 2,000, workability can optionally be prepared and it is technically advantageous.

The novel silicon-containing compound according to the present invention is an organic silicon compound having an alkoxysilyl-ethylene group at its terminal such as an organosilane compound and an organosiloxane compound. The organic silicon compound is used, for example, as a curing agent or a main agent (a base polymer) of a room temperature-curable organopolysiloxane composition that is cured (crosslinked) by a condensation reaction, and may be linear or branched. In addition, if it has 3 alkoxy groups such as methoxy group, etc. on the same silicon in one molecule (a=3), it is particularly useful as a curing agent or a main agent of dealcoholization type of RTV due to the presence of 3 functional alkoxysilane portions.

Further, if it is used as the crosslinking agent (the curing agent) of the room temperature-curable organopolysiloxane composition, the organic silicon compound containing an alkoxysilyl-ethylene group represented by the structural formula (1) is preferably an organosilane compound having no Si—O—Si bond portion in one molecule (i.e. a triorganosilyl group in which all silicon atoms at left end are blocked with a monovalent hydrocarbon group such as $R^2$, etc. in the structural formula (1)), a disiloxane compound (a dimer) represented by m=0 in the structural formula (2), or a low-molecular-weight siloxane oligomer with m=1 to 10 or so in the structural formula (2).

Meanwhile, if it is used as the main agent (the base polymer) of the room temperature-curable organopolysiloxane composition, the organic silicon compound containing an alkoxysilyl-ethylene group represented by the structural formula (1) is preferably linear diorganopolysiloxane with m≥20, and preferably with m≥24 or so in the structural formula (2).

<Method for Preparing Silicon-Containing Compound Having Alkoxysilyl-Ethylene Group at its Terminal>

The silicon-containing compound having an alkoxysilyl-ethylene group at its terminal of the present invention can be prepared by subjecting disiloxane having an ethynyl group at both terminals and octamethylcyclotetrasiloxane to polymerization reaction in the presence of an acid catalyst to prepare diorganopolysiloxane having an ethynyl group at both terminals, and subsequently carrying out an addition reaction of trialkoxysilane. The reaction formula is represented by, for example, the following formula [1].

wherein $R^1$ and $R^2$, "n", "m" and "a" are the same as before.

A disiloxane compound of the silicon-containing compound having an alkoxysilyl-ethylene group at its terminal of the present invention with m=0 in the structural formula (2) can be prepared, for example, by subjecting disiloxane having an ethynyl group at both terminals and alkoxysilane to addition reaction. The reaction formula is represented by, for example, the following formula [1'],

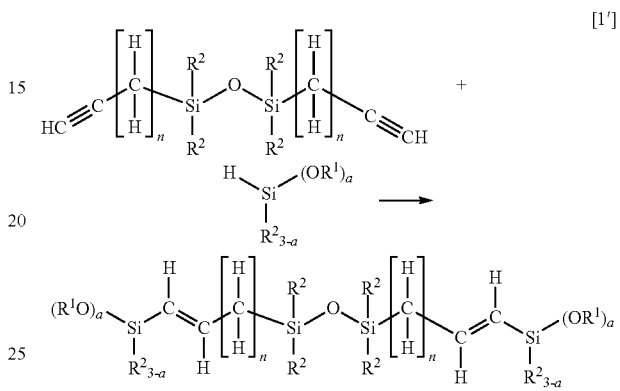

wherein $R^1$, $R^2$, "a" and "n" are the same as before.

The addition reaction catalyst may be mentioned a platinum group series catalyst, for example, a platinum series, a palladium series, and a rhodium series material, and a platinum series material is particularly suitable. The platinum series material may be exemplified by platinum black or a material in which solid platinum is carried on a carrier such as alumina, silica, etc., chloroplatinic acid, alcohol-modified chloroplatinic acid, a complex of chloroplatinic acid and an olefin, or a complex of platinum and vinylsiloxane. An amount of these platinum to be used may be the so-called catalytic amount and, for example, it may be used in an amount of 0.1 to 1,000 ppm, in terms of platinum group metal based on the amount of the trialkoxysilanes, particularly in an amount of 0.5 to 100 ppm.

The reaction is desirably carried out, in general, at a temperature of 50 to 120° C., particularly at 60 to 100° C. for 0.5 to 12 hours, particularly for 1 to 6 hours, and may be carried out without using any solvent, but a suitable solvent such as toluene, xylene, etc., may be used, if necessary, as long as it does not exert any bad effect to the addition reaction, etc.

In addition reaction to the terminal acetylene group, for example, a geometric isomer represented by the following reaction formula [2] is formed. Formation of an E isomer (a trans isomer) is highly selective and is high reactivity. However, in the silicon-containing compound of the present

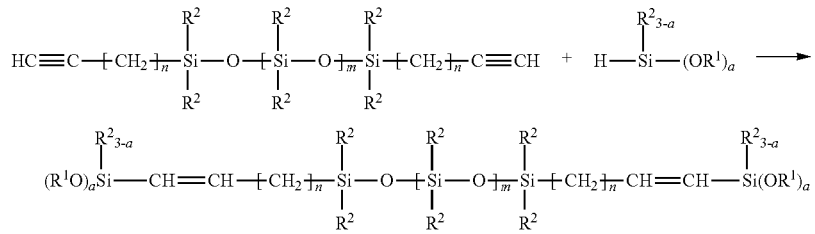

invention, it does not exert any bad effect to the characteristics, so that these isomers can be used as such without isolation thereof.

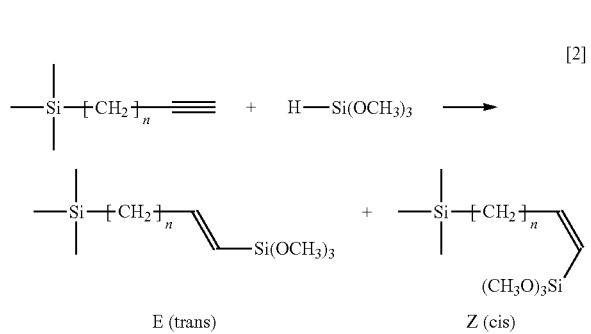

wherein, "n" are the same as before.

Illustrative example of the silicon-containing compound having an alkoxysilyl-ethylene group at its terminal includes the ones represented by the following formulae.

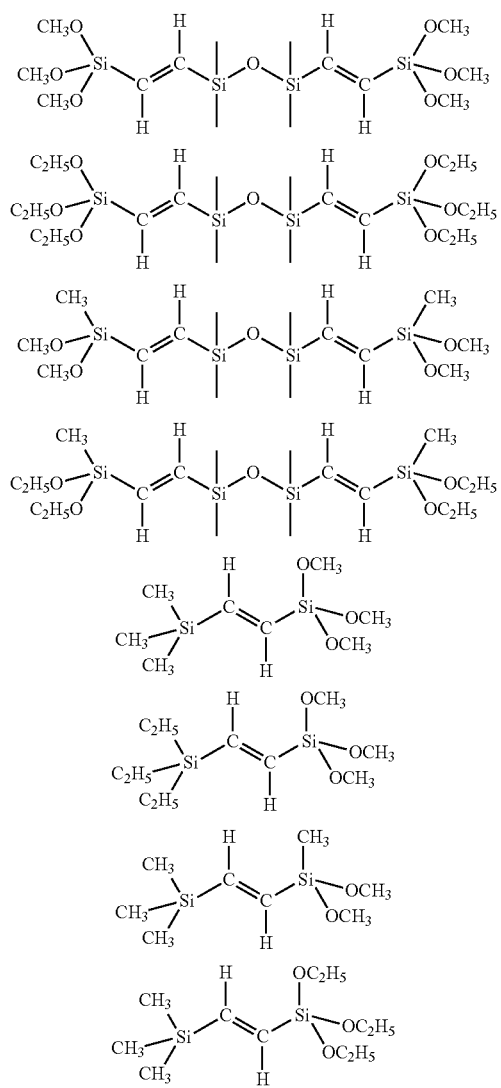

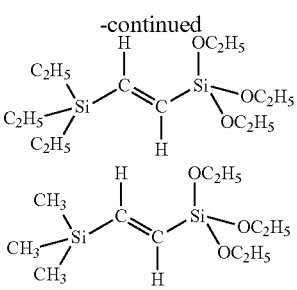

<Room Temperature-Curable Organopolysiloxane Composition>

Also, the present invention provides a room temperature-curable organopolysiloxane composition comprising:
(A) a diorganopolysiloxane comprising at least 2 silicon atoms to which a hydroxyl group and/or a hydrolyzable group are bonded in one molecule: 100 parts by mass;
(B) the silicon-containing compound having an alkoxysilyl-ethylene group at its terminal: 0.1 to 30 parts by mass;
(C) a curing catalyst: 0.001 to 15 parts by mass;
(D) a silane and/or a partial hydrolysis condensate thereof other than the component (B): 0 to 30 parts by mass;
(E) a filler: 0 to 1,000 parts by mass; and
(F) an adhesion promoter: 0 to 30 parts by mass.

The room temperature-curable organopolysiloxane composition of the present invention will be described in more detail.

[Component (A)]

The diorganopolysiloxane of a component (A) is a main agent (a base polymer) of the room temperature-curable organopolysiloxane composition of the present invention, and has at least 2 hydroxyl groups or hydrolyzable silyl groups that are bonded to silicon atoms in one molecule. Illustrative example of the diorganopolysiloxane includes linear diorganopolysiloxane both terminals of a molecular chain represented by the following general formula (2a) or (3a) of which have been blocked by hydroxyl groups that is bonded to a silicon atom (i.e. a silanol group) or a hydrolyzable silyl group,

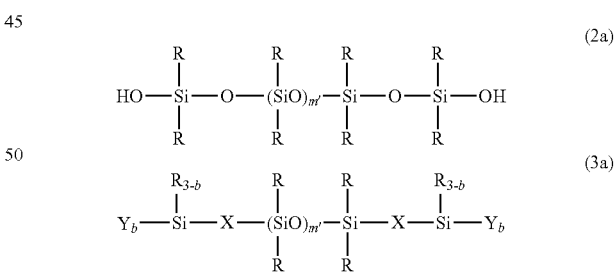

wherein R represents a substituted or unsubstituted monovalent hydrocarbon group having 1 to 12 carbon atoms, and preferably having 1 to 8 carbon atoms; X represents an oxygen atom or a divalent hydrocarbon group having 1 to 8 carbon atoms, and preferably 1 to 6 carbon atoms (for example, an alkylene group); Y represents a hydrolyzable group; "b" represents 2 or 3; "m'" represents a number which makes the viscosity of the diorganopolysiloxane at 25° C. of 100 to 1,000,000 mPa·s, usually an integer of m=20 to 2,000, preferably 22 to 1600, more preferably 23 to 1,000, and much more preferably 24 to 500.

Also, in the present invention, the degree of polymerization (or molecular weight) can be calculated, for example, as the weight average degree of polymerization (or weight average molecular weight), etc. in gel permeation chromatography (GPC) analysis by using a developing solvent such as toluene and tetrahydrofuran (THF).

In the above formula, the substituted or unsubstituted monovalent hydrocarbon group of R may be exemplified by an alkyl group such as a methyl group, an ethyl group, a propyl group, an isopropyl group, a butyl group, an isobutyl group, a tert-butyl group, a pentyl group, a hexyl group, a heptyl group, an octyl group, a nonyl group, a decyl group, an octadecyl group, etc.; a cycloalkyl group such as a cyclopentyl group, a cyclohexyl group, etc.; an alkenyl group such as a vinyl group, an allyl group, a butenyl group, a pentenyl group, a hexenyl group, etc.; an aryl group such as a phenyl group, a tolyl group, a xylyl group, an α-, β-naphthyl group, etc.; an aralkyl group such as a benzyl group, a 2-phenylethyl group, a 3-phenylpropyl group, etc.; a group in which a part or all of hydrogen atoms of these groups is/are substituted by a halogen atom such as F, Cl, Br, etc., or a cyano group, etc., for example, a 3-chloropropyl group, a 3,3,3-trifluoropropyl group, and a 2-cyanoethyl group, etc. Among these, a methyl group, an ethyl group, and a phenyl group are preferable, and a methyl group is particularly preferable.

X represents an oxygen atom or a divalent hydrocarbon group having 1 to 8 carbon atoms, and the divalent hydrocarbon group is preferably an alkylene group represented by —(CH$_2$)p- ("p" is an integer of 1 to 8). Among these, an oxygen atom or —CH$_2$CH$_2$— is preferable.

Y represents a hydrolyzable group at a terminal of a molecular chain of the above diorganopolysiloxane, and illustrative example thereof includes an alkoxy group such as a methoxy group, an ethoxy group, a propoxy group, etc.; an alkoxyalkoxy group such as a methoxyethoxy group, an ethoxyethoxy group, a methoxypropoxy group, etc.; an acyloxy group such as an acetoxy group, an octanoyloxy group, a benzoyloxy group, etc.; an alkenyloxy group such as a vinyloxy group, an isopropenyloxy group, a 1-ethyl-2-methyl vinyloxy group, etc.; a ketoxime group such as a dimethyl ketoxime group, a methylethyl ketoxime group, a diethyl ketoxime group, etc.; an amino group such as a dimethylamino group, a diethylamino group, a butylamino group, a cyclohexylamino group, etc.; an aminoxy group such as a dimethylaminoxy group, a diethylaminoxy group, etc.; and an amide group such as an N-methylacetoamide group, an N-ethylacetoamide group, an N-methylbenzamide group, etc. Among these, an alkoxy group is preferable, a methoxy group and an ethoxy group are more preferable, and a methoxy group is particularly preferable.

In the diorganopolysiloxane of the component (A), the viscosity at 25° C. is preferably 100 to 1,000,000 mPa·s, more preferably 300 to 500,000 mPa·s, particularly preferably 500 to 100,000 mPa·s, and more particularly 1,000 to 80,000 mPa·s. If the viscosity of the above diorganopolysiloxane is 100 mPa·s or more, a cured product that is excellent in physical and mechanical strength can be obtained, and if the viscosity is 1,000,000 mPa·s or less, the viscosity of the composition does not become too high, thereby causing no possible deterioration of workability in use. Herein, the viscosity refers to the number indicated on a rotary viscometer (for example, BL-type, BH-type, BS-type, and cone plate-type), etc.

Illustrative example of the diorganopolysiloxane of the component (A) includes the ones represented by the following formulae,

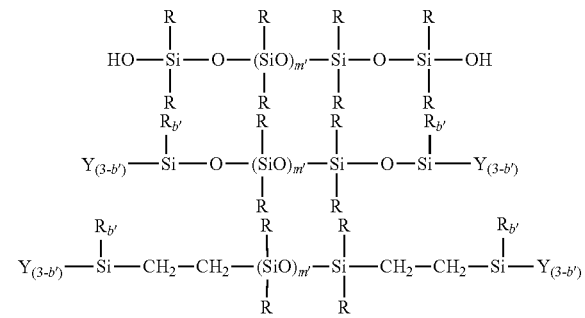

wherein, "m'", R and Y are the same as before; and "b'" is 0 or 1.

Diorganopolysiloxane of the component (A) can be used alone or in combination with two or more types thereof having a different structure or degree of polymerization.

[Component (B)]

The silicon compound containing an alkoxysilyl-ethylene group as the component (B) is a particularly important factor in the room temperature-curable organopolysiloxane composition of the present invention, and functions as a cross-linking agent (a curing agent). As such, in the above described silicon-containing organic silicon compound having an alkoxysilyl-ethylene group at its terminal, an organosilane compound (i.e. a compound having a triorganosilyl group silicon atom of a left end of which has been blocked by 3 monovalent hydrocarbon groups in the formula (1)), or a disiloxane compound with m=0 in the formula (2), or a low-molecular-weight siloxane oligomer with m=1 to 10 or so in the formula (2) can be used. The method for preparing the same is shown as above.

In addition, when the above described silicon-containing organic silicon compound having an alkoxysilyl-ethylene group at its terminal is used as the component (B) of the room temperature-curable organopolysiloxane composition, an E isomer (a trans isomer) in the reaction formula [2] is preferably used due to high reactivity.

A formulation amount of the component (B) is preferably 0.1 to 30 parts by mass, particularly 0.5 to 20 parts by mass, based on 100 parts by mass of the organopolysiloxane of the above component (A).

[Component (C)]

The component (C) is a curing catalyst, which is used to cure the composition. The organic metal catalyst may be exemplified by an alkyltin ester compound such as dibutyltin diacetate, dibutyltin dilaurate, dibutyltin dioctoate, etc.; a titanate or a titanium chelate compound such as tetraisopropoxy titanium, tetra-n-butoxy titanium, tetrakis(2-ethylhexoxy) titanium, dipropoxy bis(acetylacetonato) titanium, titanium isopropoxy octylene glycol, etc.; an organometallic compound such as zinc naphthenate, zinc stearate, zinc-2-ethyloctoate, iron-2-ethylhexoate, cobalt-2-ethylhexoate, manganese-2-ethylhexoate, cobalt naphthenate, an alkoxy aluminum compound, etc.; aminoalkyl group-substituted alkoxysilane such as 3-aminopropyltriethoxysilane, N-β (aminoethyl) γ-aminopropyltrimethoxysilane, etc.; an amine compound and a salt thereof such as hexylamine and dodecylamine phosphate, etc.; a quaternary ammonium salt such as benzyl triethyl ammonium acetate, etc.; a lower aliphatic acid salt of an alkali metal such as potassium acetate, sodium acetate, lithium oxalate, etc.; a dialkylhydroxylamine such as dimethylhydroxylamine, diethylhydroxylamine, etc.; a silane or siloxane having a guanidyl group such as tetramethylguanidylpropyltrimethoxysilane, tetramethylguanidylpropylmethyldimethoxysilane, tetramethylguanidylpropyltris(trimethylsiloxy)silane, etc., but these are not limited to one type and may be used as a mixture consisting of two or more types thereof.

A formulation amount of the curing catalyst is 0.001 to 15 parts by mass, and particularly 0.01 to 10 parts by mass, based on 100 parts by mass of the organopolysiloxane of the above component (A).

[Component (D)]

A silane and/or a partial hydrolysis condensate thereof other than the component (B) as the component (D) is a crosslinking agent. Illustrative example thereof includes ethylsilicate, propylsilicate, methyltrimethoxysilane, methyltriethoxysilane, vinyltrimethoxysilane, vinyltriethoxysilane, methyltris(methoxyethoxy)silane, vinyltris(methoxyethoxy)silane, methyltripropenoxysilane, etc. and a partial hydrolysis condensate thereof. These can be used alone or in combination with two or more types thereof.

In the present invention, a partial hydrolysis condensate means a siloxane oligomer having at least 2, preferably 3 or more residual hydrolyzable groups in one molecule which is formed by partially hydrolyzing and condensing the hydrolyzable silanes.

A formulation amount of the component (D) is normally 0 to 30 parts by mass, preferably 0.1 to 20 parts by mass, and more preferably 0.5 to 15 parts by mass, based on 100 parts by mass of the above component (A). If the formulation amount is over 30 parts by mass, a cured product is too hard and economically disadvantage.

[Component (E)]

The component (E) is a filler, which is used to provide a sufficient mechanical strength to a cured product formed from the composition. The filler may be used those well-known in the art and may be mentioned, for example, dry silica such as calcined silica, pulverized silica, aerosol silica (fumed silica), silica aerogel, etc.; wet silica such as precipitated silica sol-gel method silica, etc.; reinforcing silica type fine powder such as diatomaceous earth, etc.; metal oxide such as iron oxide, zinc oxide, titanium oxide, etc.; a material in which the surface of the above is subjected to hydrophobic treatment by an organosilane or an organosilazane, etc.; metal carboxylate such as calcium carbonate, magnesium carbonate, zinc carbonate, etc.; asbestos, glass wool, carbon black, finely particle mica, fused silica powder (quartz powder), synthetic resin powder of a polystyrene, a polyvinyl chloride, a polypropylene, etc.

A formulation amount of the filler is preferably 0 to 1,000 parts by mass, and particularly 1 to 400 parts by mass, based on 100 parts by mass of the component (A). A cured product obtained from the composition shows sufficient mechanical strength when the filler is blended than when the filler is not blended. If the filler is used in larger quantities than 1,000 parts by mass, the viscosity of the composition increases to deteriorate workability and decrease rubber strength after being cured, thereby making it hard to obtain sufficient rubber elasticity.

[Component (F)]

The component (F) is an adhesion promoter, which is used to provide sufficient adhesiveness to a cured product formed from the composition.

In particular, aminosilanes such as γ-aminopropyltriethoxysilane, 3-2-(aminoethylamino) propyltrimethoxysilane, etc.; epoxy silanes such as a γ-glycidoxypropyltrimethoxysilane, a β-(3,4-epoxycyclohexyl) ethyltrimethoxysilane, etc.; and isocyanatesilanes are preferably formulated. An amount of these adhesion promoters is preferably 0 to 30 parts by mass, and particularly 0.1 to 20 parts by mass, based on 100 parts by mass of the organopolysiloxane of component (A).

[Other Components]

As an additive, a conventionally known additive, such as a pigment, a dye, antiaging agent, an antioxidant, an antistatic agent, a flame retardant such as antimony oxide, and paraffin chloride, etc. may be formulated in the room temperature curable composition of the present invention. Further, a polyether as a thixotropic property improver, an antifungal agent, an antimicrobial agent, may be formulated.

The room temperature curable composition of the present invention can be obtained by uniformly mixing the predetermined amounts of the respective components, and the predetermined amounts of the respective additives in a dry atmosphere.

In addition, the room temperature curable composition of the present invention is cured by allowing to stand at room temperature, and the molding methods and the curing conditions, etc., may be employed the conventionally known method and conditions depending on the kind of the composition.

The thus obtained room temperature curable composition of the present invention forms a rubber elastomer cured product that is excellent in heat resistance, weather resistance, and low temperature characteristics, and adhesiveness to the various kinds of substrate materials, particularly to a metal by being rapidly cured at room temperature by the moisture in the air. In addition, the composition of the present invention provides a cured product that is particularly excellent in storage stability and curability and physical properties as described above by being rapidly cured when exposed to the air even after storage of 12 months. In particular, it does not discharge any poisonous or corrosive gas at the time of curing, so that no patina is formed at the surface onto which the composition has been applied. In particular, the composition never causes contact fault of electric and electronic parts, so that it is useful not only as an insulating material or an adhesive for electric and electronic parts, but also may be widely used as a sealing agent, a coating agent, a covering agent, a releasing agent to the various kinds of substrates, and as a fiber treatment agent as well.

EXAMPLES

In the following, the present invention will be described with reference to the Examples and Comparative Examples, but it is not limited by the following Examples. Incidentally, in the following examples, all the "parts" mean "parts by mass", and the viscosity shows the value measured by rotary viscometer at 25° C.

Synthesis Example 1

Synthesis of Trimethoxysilyl-Ethylene-Substituted Trimethylsilane

Figure 2:
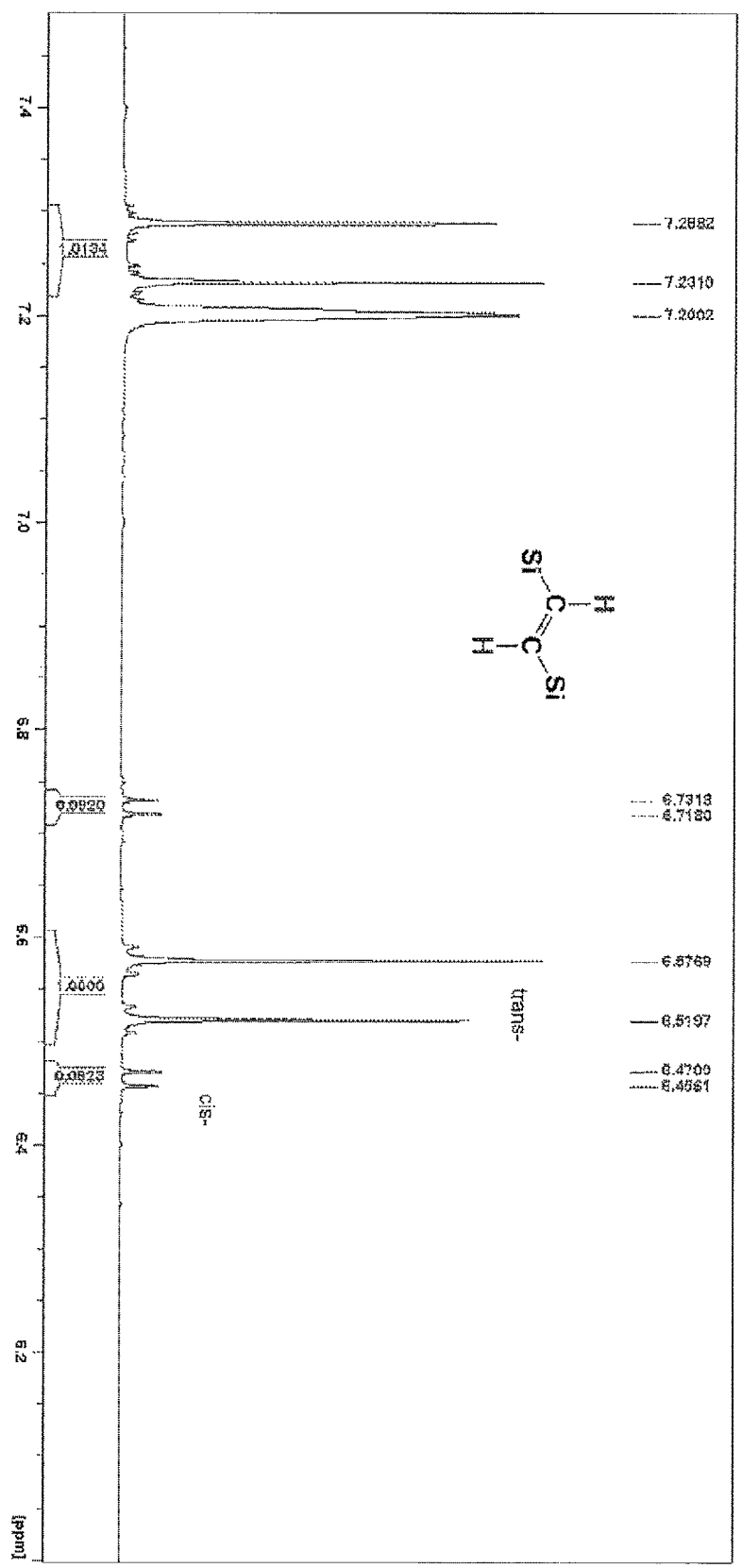
FIG. 2 shows an enlarged $^1$H-NMR-chart (6.0 to 7.5 ppm or so) of a compound 1 obtained in a Synthesis Example 1 (a trimethoxysilyl-ethylene-substituted trimethylsilane)

Ethynyltrimethylsilane (98.2 g) (1.0 mol) and a 0.5 wt % toluene solution of chloroplatinic acid ($H_2PtCl_6 \cdot 6H_2O$) (0.5 g) were fed into a 250 mL four necked separable flask equipped with a mechanical stirrer, a thermometer and a dropping funnel, and trimethoxysilane (128.3 g) (1.05 mol) was dropped therein at 85° C. for approximately 2 hours. Thereafter, the mixture was stirred at 90° C. for 1 hour and distilled to obtain trimethoxysilyl-ethylene-substituted trimethylsilane (compound 1) shown as follows (213 g) (yield:

97%). A ¹H-NMR-chart of the compound was examined to confirm a trimethoxysilyl-ethylene-substituted trimethylsilane compound as a target compound (FIGS. 1 to 2, trans-:cis-=91:9). The reaction formula is represented by the following formula [3].

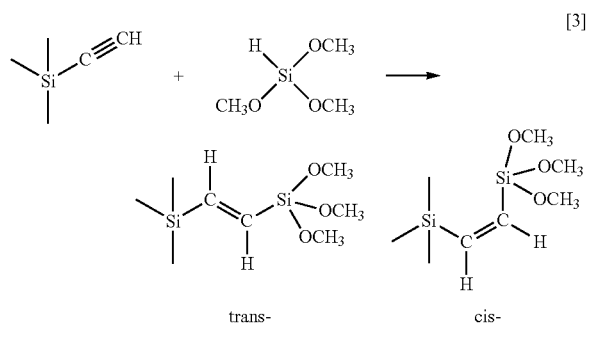

Synthesis Example 2

Figure 3:
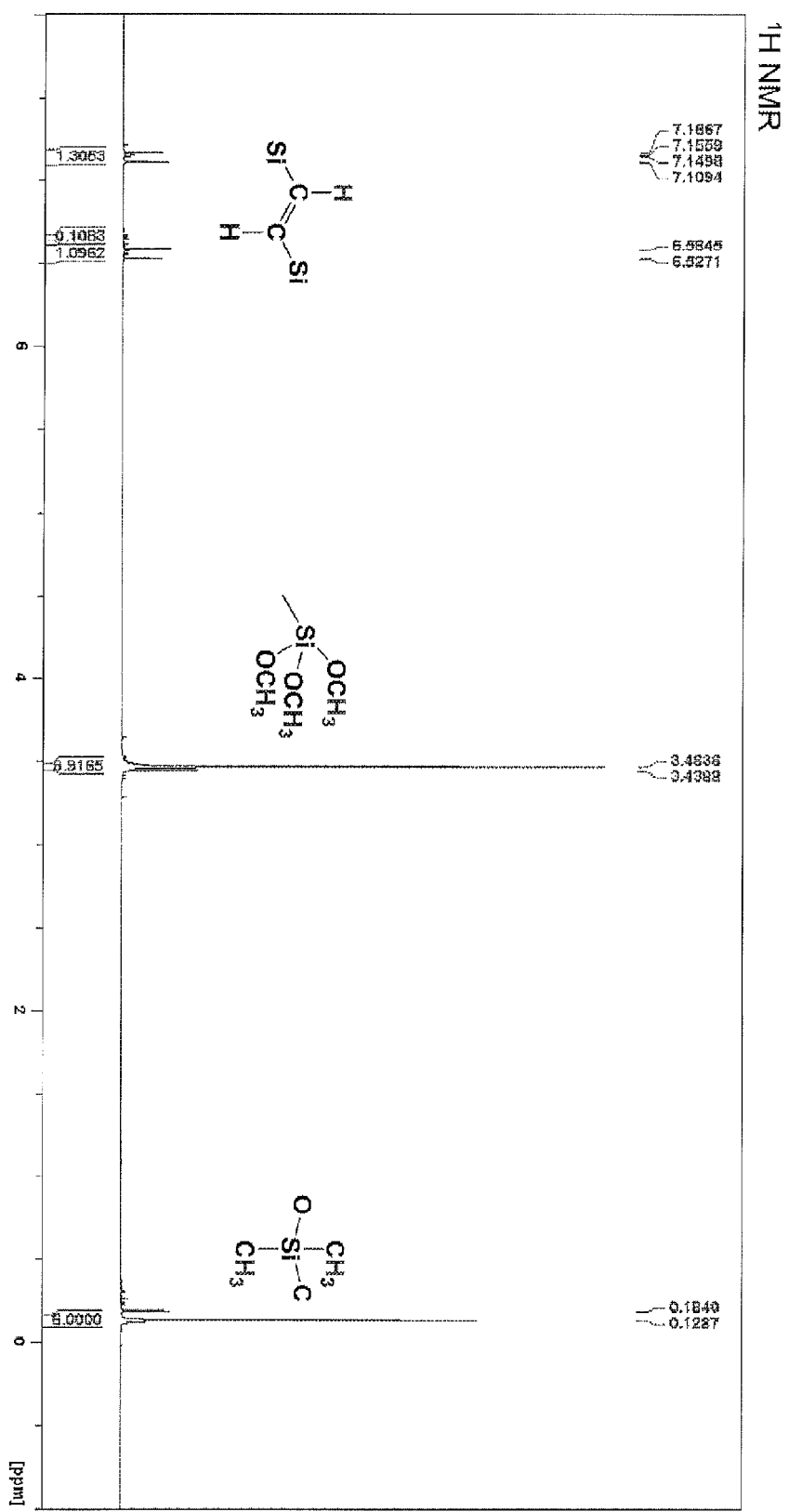
FIG. 3 shows a $^1$H-NMR-chart of a compound 2 obtained in a Synthesis Example 2 (a tetramethoxydisiloxane having a trimethoxysilyl-ethylene group at both terminals)
Figure 4:
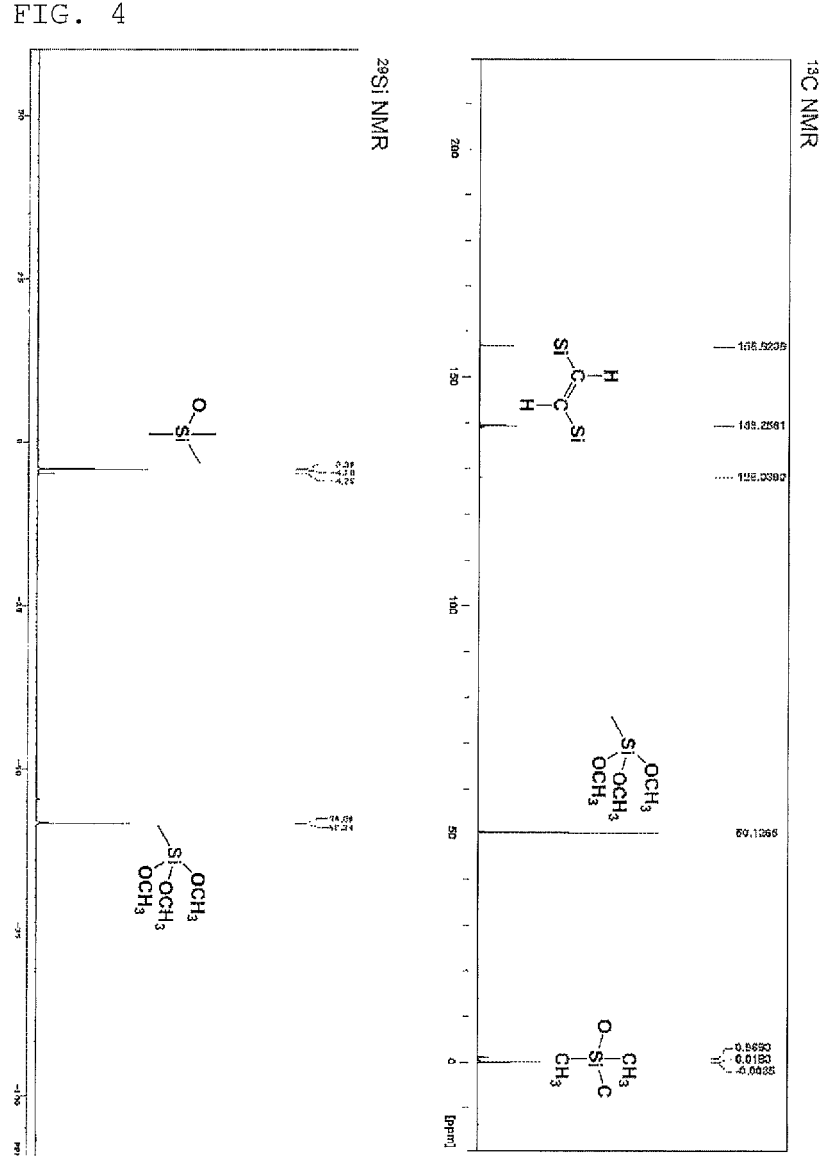
FIG. 4 shows a $^{13}$C-NMR-chart and a $^{29}$Si—NMR-chart of a compound 2 obtained in a Synthesis Example 2 (a tetramethoxydisiloxane having a trimethoxysilyl-ethylene group at both terminals)

Synthesis of Tetramethyldisiloxane Having a Trimethoxysilyl-Ethylene Group at Both Terminals 1,3-diethynyl-1,1,3,3-tetramethyldisiloxane (100 g) (0.55 mol), a 0.5 wt % toluene solution of chloroplatinic acid ($H_2PtCl_6 \cdot 6H_2O$) (0.5 g) and 50 mL of toluene were fed into a 500 mL four necked separable flask equipped with a mechanical stirrer, a thermometer and a dropping funnel, and trimethoxysilane (160 g) (1.31 mol) was dropped therein at 85° C. for approximately 1 hour. Thereafter, the mixture was stirred at 90° C. for 4 hours and distilled to obtain a compound 2 (226 g) (yield: 96%) as shown above. A ¹H-NMR-chart of the compound was examined to confirm a tetramethoxydisiloxane having a trimethoxysilyl-ethylene group at both terminals (compound 2) as a target compound (FIGS. 3 to 4, trans-:cis-=91:9). The reaction formula is represented by the following formula [4].

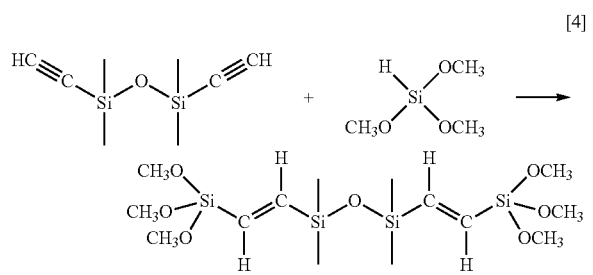

Synthesis Example 3

Figure 5:
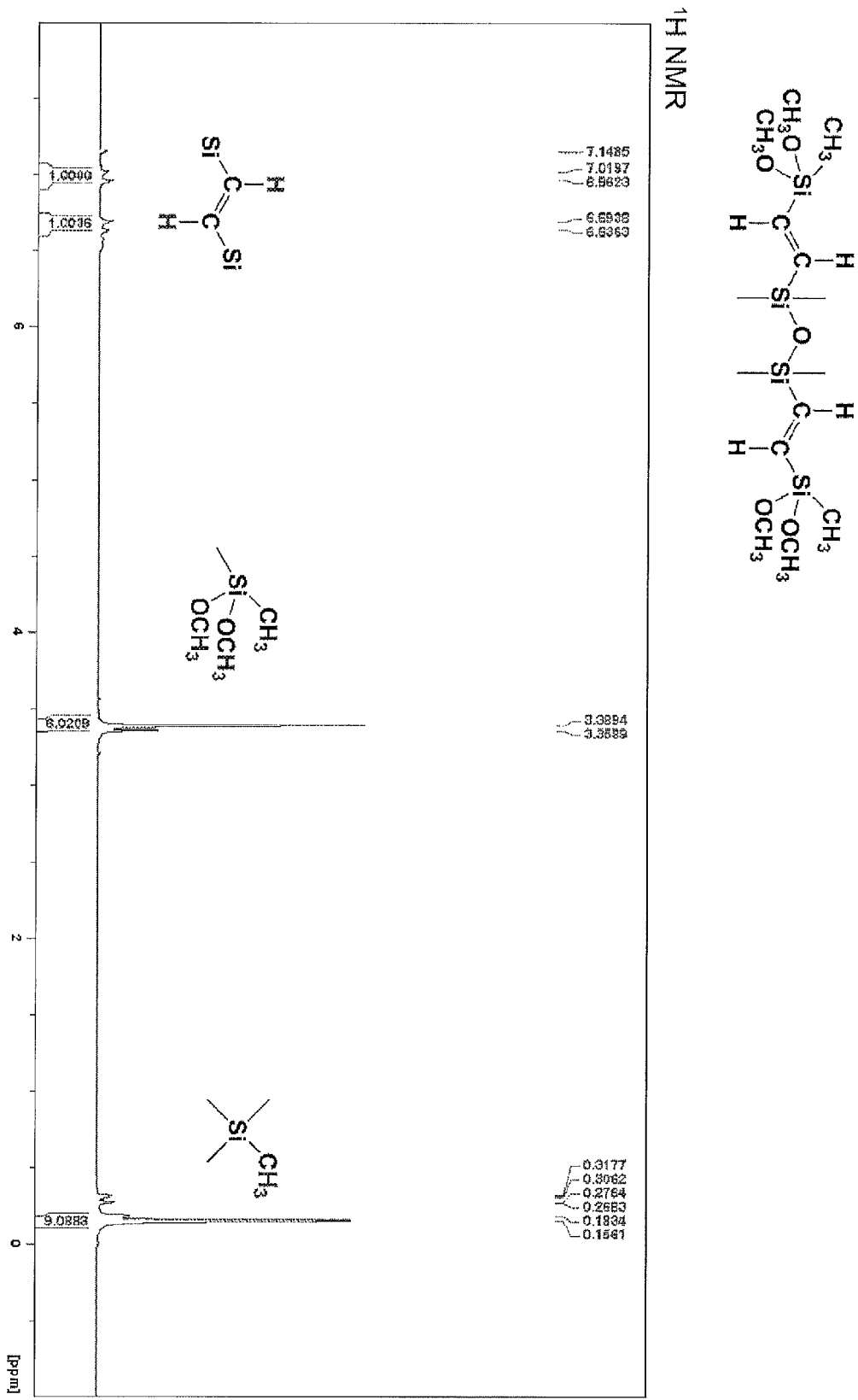
FIG. 5 shows a $^1$H-NMR-chart of a compound 3 obtained in a Synthesis Example 3 (a tetramethoxydisiloxane having a dimethoxymethylsilyl-ethylene group at both terminals)

Synthesis of Tetramethyldisiloxane Having a Dimethoxymethylsilyl-Ethylene Group at Both Terminals 1,3-diethynyl-1,1,3,3-tetramethyldisiloxane (17.0 g) (0.094 mol), a 0.5 wt % toluene solution of chloroplatinic acid ($H_2PtCl_6 \cdot 6H_2O$) (0.05 g) and 10 mL of toluene were fed into a 500 mL four necked separable flask equipped with a mechanical stirrer, a thermometer and a dropping funnel, and dimethoxymethylsilane (19.9 g) (0.187 mol) was dropped therein at 85° C. for approximately 10 minutes. Thereafter, the mixture was stirred at 90° C. for 4 hours and distilled to obtain a compound 3 as shown above (29.4 g) (yield: 80%). A ¹H-NMR-chart of the compound was examined to confirm a tetramethoxydisiloxane having a dimethoxymethylsilyl-ethylene group at both terminals (compound 3) as a target compound (FIG. 5, trans-:cis-=89:11). The reaction formula is represented by the following formula [5].

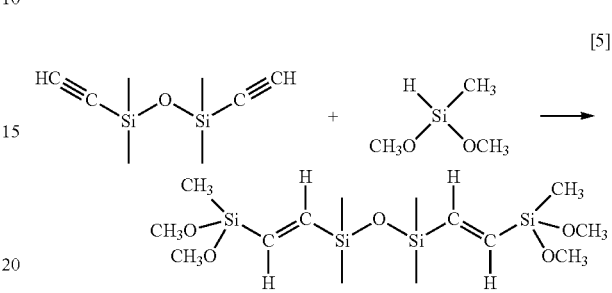

Example 1

40 parts of linear dimethylpolysiloxane both terminals of a molecular chain of which have been blocked by hydroxyl groups (silanol groups) and having a viscosity of 700 mPa·s and 60 parts of linear dimethylpolysiloxane both terminals of a molecular chain of which have been blocked by hydroxyl groups and having a viscosity of 5,000 mPa·s were mixed, and subsequently 5.2 parts of the compound 1 as a crosslinking agent (a curing agent) and 0.75 parts of tetramethylguanidylpropyltrimethoxysilane were added, and mixed until the mixture became uniform under shielding moisture to prepare a composition.

Example 2

5.0 parts of a compound 2 was used in place of the compound 1 in Example 1 to prepare a composition. Other conditions were the same.

Example 3

4.6 parts of a compound 3 was used in place of the compound 1 in Example 1 to prepare a composition. Other conditions were the same.

Comparative Example 1

5.2 parts of the following compound 4 was used in place of the compound 1 in Example 1 to prepare a composition. Other conditions were the same.

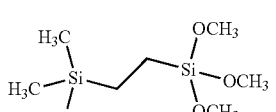

Compound 4

Comparative Example 2

4.9 parts of the following compound 5 was used in place of the compound 1 in Example 1 to prepare a composition. Other conditions were the same.

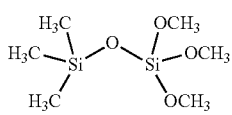

Compound 5

Comparative Example 3

3.5 parts of vinyltrimethoxysilane was used in place of the compound 1 in Example 1 to prepare a composition. Other conditions were the same.

Comparative Example 4

3.2 parts of methyltrimethoxysilane was used in place of the compound 1 in Example 1 to prepare a composition. Other conditions were the same.

Comparative Example 5

5.3 parts of vinyltrisisopropenoxysilane was used in place of the compound 1 in Example 1 to prepare a composition. Other conditions were the same.

Subsequently, the respective compositions immediately after preparation which were prepared in the Examples 1 to 3 and the Comparative Examples 1 to 5 were each extruded to a sheet state with a thickness of 2 mm, exposed to air at 23° C., 50% RH, then, the each sheet was allowed to stand under the same atmosphere for 7 days to obtain a cured product. Physical properties (initial physical properties) of the cured product were measured in accordance with JIS K-6249. The hardness was measured by using a durometer A hardness meter according to JIS K-6249.

Further, the cured product was stored in a thermo-hygrostat at 85° C., 85% RH for 500 hours and the physical properties were similarly measured. Thereafter, the same measurements were carried out with regard to the sheets each having a thickness of 2 mm which had been prepared from the respective compositions immediately after preparation which were prepared in the Examples and the Comparative Examples each charged in a sealed vessel and allowed to stand at a temperature of 70° C. for 7 days The respective compositions was filled in a glass container (28 mm in internal diameter and 15 mm deep), exposed to air at 23° C., 50% RH for 8 hours, 24 hours, and 120 hours. Thereafter, the thickness that was cured from a portion that contacted the air was measured (cured film thickness).

The respective compositions immediately after preparation which were prepared in the Examples and the Comparative Examples was fed into a sealed vessel and allowed to stand at a temperature of 150° C. for 4 days to obtain a sheet. The state of the cured sheet was confirmed (high sealing heat resistance test).

The results are shown in Table 1.

TABLE 1

|  |  | Example 1 | Example 2 | Example 3 |
|---|---|---|---|---|
| Initial | Hardness (durometer A) | 19 | 26 | 17 |
|  | Elongation (%) at breakage | 120 | 95 | 130 |
|  | Tensile strength (MPa) | 0.31 | 0.42 | 0.17 |
| Durability test 85° C., 85% RH | Hardness (durometer A) | 15 | 20 | 14 |
|  | Elongation (%) at breakage | 225 | 120 | 160 |
|  | Tensile strength (MPa) | 0.20 | 0.30 | 0.14 |
| Storage test 70° C., 7 days | Hardness (durometer A) | 17 | 21 | 14 |
|  | Elongation (%) at breakage | 130 | 105 | 160 |
|  | Tensile strength (MPa) | 0.32 | 0.37 | 0.18 |
| Cured film thickness | 8 hours (mm) | 1.2 | 2.1 | 1.9 |
|  | 24 hours (mm) | 2.0 | 3.5 | 3.3 |
|  | 120 hours (mm) | 6.6 | 7.7 | 7.2 |
| High sealing heat resistance test | State of curing | Cured | Cured | Cured |

|  |  | Comparative Example 1 | Comparative Example 2 | Comparative Example 3 |
|---|---|---|---|---|
| Initial | Hardness (durometer A) | 7 | 10 | 22 |
|  | Elongation (%) at breakage | 200 | 180 | 115 |
|  | Tensile strength (MPa) | 0.15 | 0.21 | 0.30 |
| Durability test 85° C., 85% RH | Hardness (durometer A) | Not measured | 4 | 5 |
|  | Elongation (%) at breakage | 170 | 220 | 260 |
|  | Tensile strength (MPa) | 0.16 | 0.12 | 0.15 |
| Storage test 70° C., 7 days | Hardness (durometer A) | 4 | 6 | 18 |
|  | Elongation (%) at breakage | 250 | 200 | 120 |
|  | Tensile strength (MPa) | 0.13 | 0.18 | 0.28 |
| Cured film thickness | 8 hours (mm) | Uncured | Uncured | Uncured |
|  | 24 hours (mm) | Uncured | 1.2 | 1.8 |
|  | 120 hours (mm) | Uncured | 5.2 | 6.8 |
| High sealing heat resistance test | State of curing | Not cured | Not cured | Not cured |

|  |  | Comparative Example 4 | Comparative Example 5 |
|---|---|---|---|
| Initial | Hardness (durometer A) | 8 | 22 |
|  | Elongation (%) at breakage | 210 | 100 |
|  | Tensile strength (MPa) | 0.18 | 0.28 |

TABLE 1-continued

| | | | |
|---|---|---|---|
| Durability test 85° C., 85% RH | Hardness (durometer A) | Not measured | 5 |
| | Elongation (%) at breakage | 290 | 170 |
| | Tensile strength (MPa) | 0.08 | 0.10 |
| Storage test 70° C., 7 days | Hardness (durometer A) | 5 | 19 |
| | Elongation (%) at breakage | 230 | 120 |
| | Tensile strength (MPa) | 0.17 | 0.28 |
| Cured film thickness | 8 hours (mm) | Uncured | 1.5 |
| | 24 hours (mm) | Uncured | 2.1 |
| | 120 hours (mm) | 6.9 | 6.9 |
| High sealing heat resistance test | State of curing | Not cured | cured |

From the result shown in Table 1, it would be clear that the Example 1 is higher rapid curability and durability than the corresponding Comparative Examples 1 to 4. Also, it would be clear that the Examples 2 and 3 are more excellent durability than the Comparative Example 5. Also, it would be clear that the Examples 1 to 3 are higher storage stability than the Comparative Examples.

Synthesis Example 4

Figure 6:
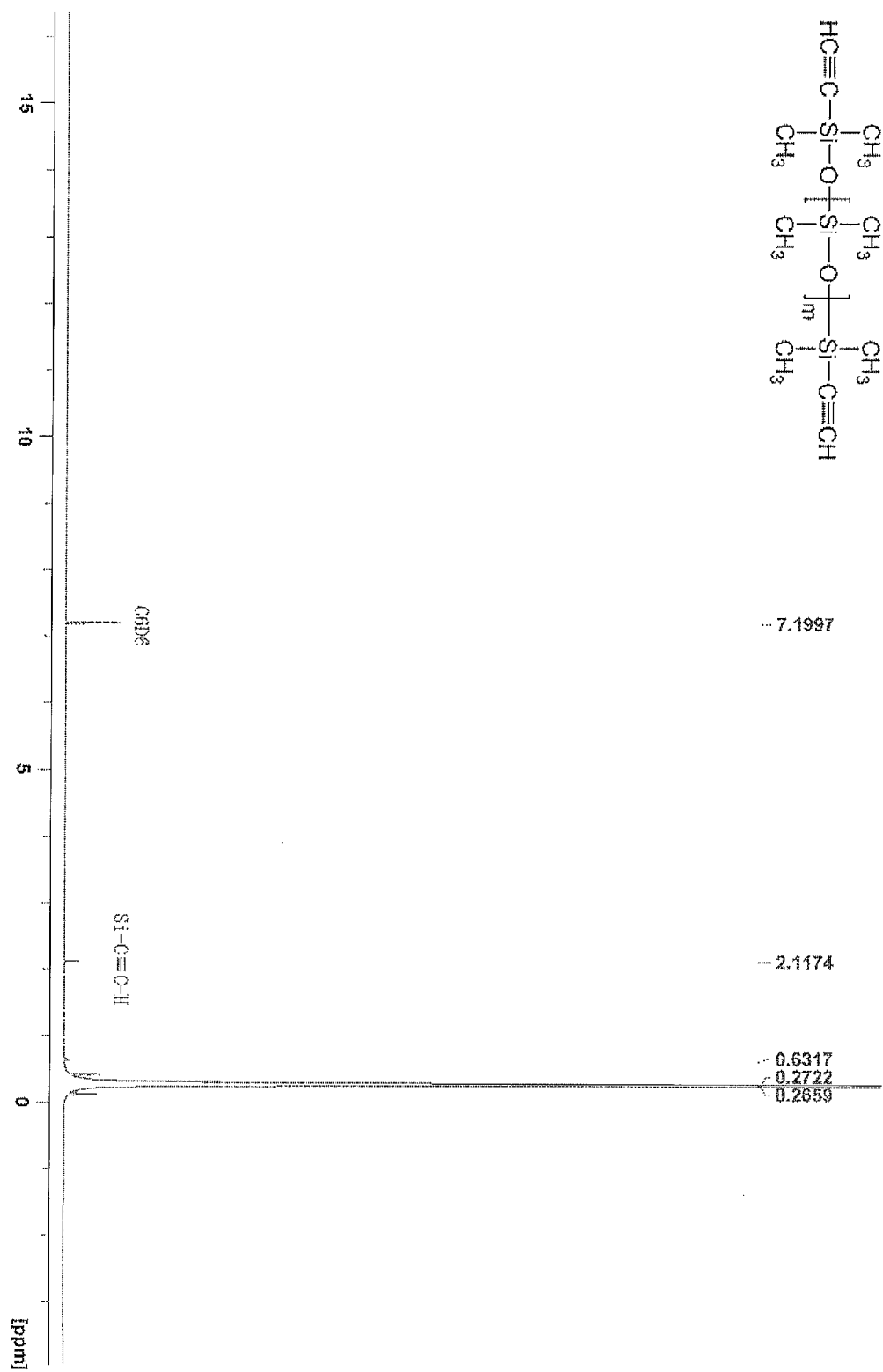
FIG. 6 shows a $^1$H-NMR-chart of a raw material used in Synthesis Example 4 (a organopolysiloxane compound containing an ethynyl group at its terminals)

A polyorganosiloxane compound containing an ethynyl group at both terminals of a molecular chain (1,500 g) (0.16 mol in terms of to the amount of a functional group of an ethynyl group of a terminal) and a platinum catalyst (0.35 g) were fed into a 3,000 mL four necked flask equipped with a mechanical stirrer, a reflux cooling pipe, a thermometer and a dropping funnel to be heated up to 75° C. and stirred. Herein, a $^1$H-NMR-chart of a substance used as the polyorganosiloxane compound containing an ethynyl group at both terminals of a molecular chain was examined to confirm the polyorganosiloxane compound containing an ethynyl group at both terminals of a molecular chain (FIG. 6).

Figure 7:
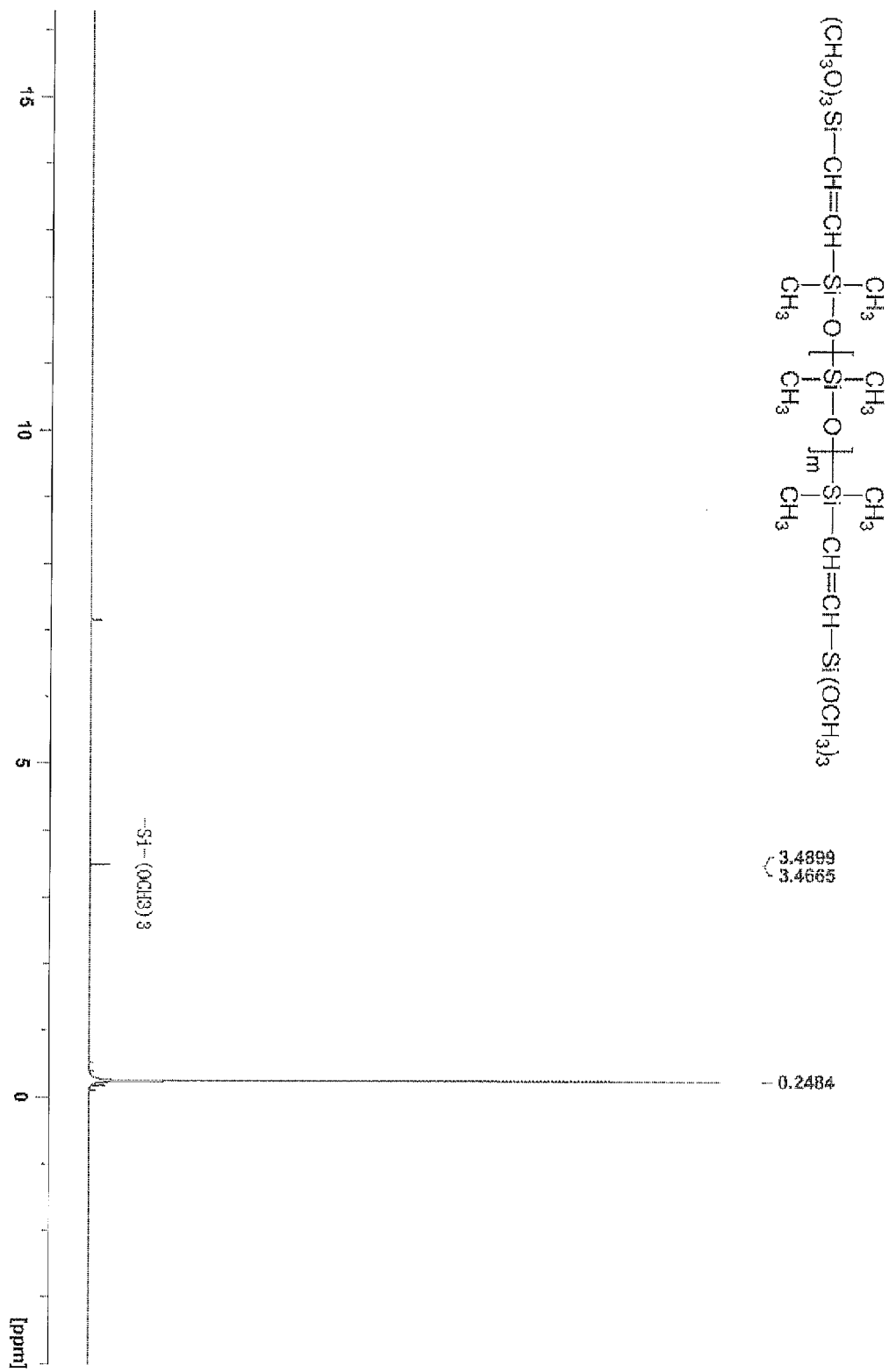
FIG. 7 shows a $^1$H-NMR-chart of a target compound obtained in Synthesis Example 4 (an organosiloxane compound having a trimethoxysilyl-ethylene group at its terminals)
Figure 8:
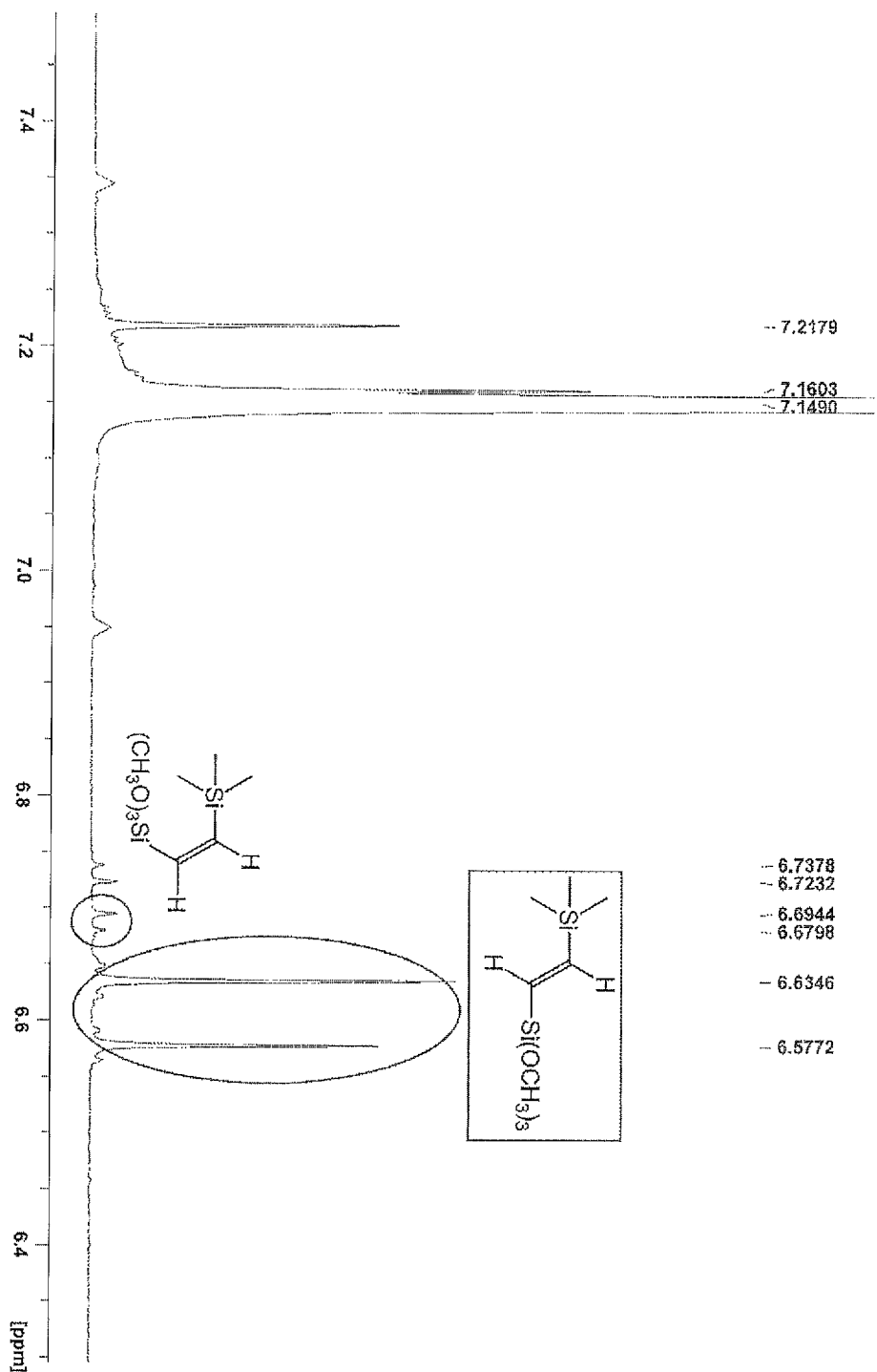
FIG. 8 shows an enlarged $^1$H-NMR-chart (6.4 to 7.4 ppm or so) of a target compound obtained in Synthesis Example 4 (an organosiloxane compound having a trimethoxysilyl-ethylene group at its terminals).

Subsequently, when trimethoxysilane (22.4 g) (0.18 mol) was and dropped with stirring, the product was heated with a reaction temperature of 80 to 85° C. to hold a reaction system for 6 hours within this temperature range. After completion of the reaction, a small excess of trimethoxysilane was removed under reduced pressure. After cooling the product down to room temperature, it was filtered to obtain a polyorganosiloxane compound having a trimethoxysilyl-ethylene group at its terminals (1,450 g) (viscosity of 970 mPa·s). A $^1$H-NMR-chart of the compound was examined to confirm a polyorganosiloxane compound having a trimethoxysilyl-ethylene group at both terminals of a molecular chain as a target compound (FIGS. 7 and 8). The reaction formula is represented by the following formula [6].

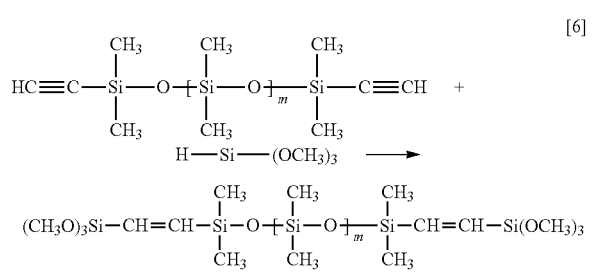

[6]

wherein "m" represents 280.

Example 4

100 parts of polydimethylsiloxane both terminals of a molecular chain of which have been blocked by trimethoxysilyl-ethylene groups and having a viscosity of 970 mPa·s synthesized according to the method of Synthesis Example 4 was mixed with 0.1 parts of titaniumtetraisopropoxide until the mixture became uniform under shielding moisture to prepare a composition.

Example 5

100 parts of polydimethylsiloxane (base polymer) both terminals of a molecular chain of which have been blocked by trimethoxysilyl-ethylene groups and having a viscosity of 970 mPa·s was mixed with 0.2 parts of titaniumtetra-2-ethylhexoxide until the mixture became uniform under shielding moisture to prepare a composition.

Example 6

100 parts of polydimethylsiloxane both terminals of a molecular chain of which have been blocked by trimethoxysilyl-ethylene groups and having a viscosity of 970 mPa·s was mixed with 0.5 parts of titanium diisopropoxybis(ethylacetoacetate) until the mixture became uniform under shielding moisture to prepare a composition.

Example 7

100 parts of polydimethylsiloxane both terminals of a molecular chain of which have been blocked by trimethoxysilyl-ethylene groups and having a viscosity of 970 mPa·s was mixed with 0.3 parts of dioctyltin dilaurate until the mixture became uniform under shielding moisture to prepare a composition.

Example 8

100 parts of polydimethylsiloxane the terminal of a molecular chain of which have been blocked by trimethoxysilyl-ethylene groups and having a viscosity of 970 mPa·s was mixed with 0.2 parts of diazabicycloundecene until the mixture became uniform under shielding moisture to prepare a composition.

Comparative Examples 6 to 10

100 parts of polydimethylsiloxane represented by the following structural formula (3) the terminals of a molecular chain of which have been blocked by trimethoxysilylethyl groups was used in place of 100 parts of polydimethylsiloxane the terminals of a molecular chain of which have been blocked by trimethoxysilyl-ethylene groups in Examples 4 to 8 to prepare a composition. Other conditions were the same,

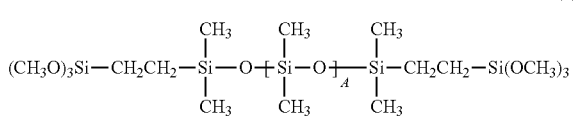

(3)

wherein A represents 280.

Comparative Examples 11 to 15

100 parts of polydimethylsiloxane represented by the following structural formula (4) the terminals of a molecular chain of which have been blocked by trimethoxysiloxy groups was used in place of 100 parts of polydimethylsiloxane the terminals of a molecular chain of which have been blocked by trimethoxysilyl-ethylene groups in Examples 4 to 8 to prepare a composition. Other conditions were the same,

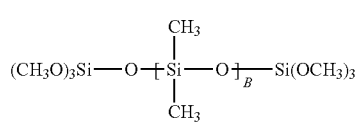

(4)

wherein B represents 270.

Subsequently, the respective compositions immediately after preparation which were prepared in the Examples and the Comparative Examples were each extruded to a sheet state with a thickness of 2 mm, exposed to air at room temperature (23° C.), 50% RH, then, the each sheet was allowed to stand under the same atmosphere for 7 days to obtain a cured product. Physical properties (initial physical properties) of the cured product were measured in accordance with JIS K-6249. The hardness was measured by using a durometer A hardness meter according to JIS K-6249.

Further, the cured product was allowed to stand at 85° C., 85% RH in a thermo-hygrostat for 7 days and the physical properties were similarly measured. Thereafter, the respective compositions immediately after preparation which were prepared in the Examples and the Comparative Examples was fed into a sealed vessel, and stored at 70° C. for 7 days to obtain a sheet with a thickness of 2 mm. Physical properties of the sheet were similarly measured.

The results are shown in Tables 2 and 3.

TABLE 2

|  | Example 4 | Example 5 | Example 6 | Example 7 | Example 8 |
|---|---|---|---|---|---|
| Tack free time | 6 | 6 | 3 | 8 | 3 |

|  | Comparative Example 6 | Comparative Example 7 | Comparative Example 8 | Comparative Example 9 | Comparative Example 10 |
|---|---|---|---|---|---|
| Tack free time | 240 | 120 | 60 | 300 | 360 or more |

|  | Comparative Example 11 | Comparative Example 12 | Comparative Example 13 | Comparative Example 14 | Comparative Example 15 |
|---|---|---|---|---|---|
| Tack free time | 210 | 150 | 120 | 240 | 60 |

TABLE 3

|  |  | Example 4 | Example 5 | Example 6 | Example 7 | Example 8 |
|---|---|---|---|---|---|---|
| Initial | Hardness (durometer A) | 33 | 31 | 33 | 26 | 26 |
|  | Elongation (%) at breakage | 75 | 125 | 100 | 90 | 76 |
|  | Tensile strength (MPa) | 0.42 | 0.58 | 0.52 | 0.36 | 0.38 |
| Durability test 85° C., 85% RH 7 days | Hardness (durometer A) | 30 | 30 | 31 | 27 | 26 |
|  | Elongation (%) at breakage | 60 | 100 | 85 | 95 | 80 |
|  | Tensile strength (MPa) | 0.31 | 0.44 | 0.37 | 0.38 | 0.37 |
| Storage test 70° C., 7 days | Hardness (durometer A) | 30 | 32 | 27 | 26 | 27 |
|  | Elongation (%) at breakage | 130 | 155 | 120 | 90 | 68 |
|  | Tensile strength (MPa) | 0.42 | 0.64 | 0.39 | 0.36 | 0.34 |

|  |  | Comparative Example 6 | Comparative Example 7 | Comparative Example 8 | Comparative Example 9 | Comparative Example 10 |
|---|---|---|---|---|---|---|
| Initial | Hardness (durometer A) | 26 | 32 | 33 | 18 | 1 |
|  | Elongation (%) at breakage | 140 | 100 | 75 | 85 | 255 |

TABLE 3-continued

|  |  |  |  |  |  |  |
|---|---|---|---|---|---|---|
|  | Tensile strength (MPa) | 0.53 | 0.45 | 0.42 | 0.23 | 0.05 |
| Durability test 85° C., 85% RH 7 days | Hardness (durometer A) | 32 | 32 | 29 | 31 | 9 |
|  | Elongation (%) at breakage | 120 | 105 | 95 | 90 | 155 |
|  | Tensile strength (MPa) | 0.51 | 0.47 | 0.39 | 0.44 | 0.04 |
| Storage test 70° C., 7 days | Hardness (durometer A) | 30 | 31 | 25 | 12 | 1 |
|  | Elongation (%) at breakage | 100 | 110 | 175 | 165 | 156 |
|  | Tensile strength (MPa) | 0.37 | 0.41 | 0.45 | 0.24 | 0.04 |

|  |  | Comparative Example 11 | Comparative Example 12 | Comparative Example 13 | Comparative Example 14 | Comparative Example 15 |
|---|---|---|---|---|---|---|
| Initial | Hardness (durometer A) | 26 | 27 | 27 | 29 | 26 |
|  | Elongation (%) at breakage | 115 | 135 | 125 | 105 | 131 |
|  | Tensile strength (MPa) | 0.42 | 0.46 | 0.48 | 0.46 | 0.38 |
| Durability test 85° C., 85% RH 7 days | Hardness (durometer A) | 18 | 20 | 21 | 22 | 12 |
|  | Elongation (%) at breakage | 145 | 170 | 125 | 140 | 109 |
|  | Tensile strength (MPa) | 0.32 | 0.36 | 0.33 | 0.41 | 0.21 |
| Storage test 70° C., 7 days | Hardness (durometer A) | 25 | 26 | 20 | 30 | 22 |
|  | Elongation (%) at breakage | 150 | 175 | 235 | 90 | 87 |
|  | Tensile strength (MPa) | 0.36 | 0.42 | 0.54 | 0.43 | 0.3 |

From the result shown in Table 2, it would be clear that the Examples 4 to 8 is extremely higher rapid curability than the corresponding Comparative Examples 6 to 10 and the Comparative Examples 11 to 15. From the result shown in Table 3, it would be clear that the Example 8 is particularly higher durability and storage stability than the corresponding Comparative Examples 6 and 15.

According to the above observations, it would be clear that the room temperature curable composition of the present invention and a base polymer thereof provide a cured product having rapid curability, durability, and storage stability.

It must be stated here that the present invention is not restricted to the embodiments represented by Examples. The embodiments represented by Examples are merely examples so that any embodiments consisting of substantially the same technical concept as disclosed in the claims of the present invention and expressing a similar effect are included in the technical scope of the present invention.

The invention claimed is:

1. A silicon-containing compound having an alkoxysilyl-ethylene group at its terminal which comprises at least one silyl-ethylene bond represented by the following structural formula (a) in one molecule,

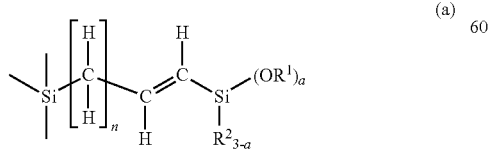

(a)

wherein $R^1$ represents a monovalent hydrocarbon group having 1 to 20 carbon atoms which may have a substituent, and those having 3 or more carbon atoms among the hydrocarbon groups may be a cycloalkyl group which is cyclic; $R^2$ represents a hydrogen atom, or a monovalent hydrocarbon group having 1 to 20 carbon atoms which may have a substituent; "a" represents an integer of 1 to 3; two out of three bonds attached to Si on the left part of formula (a) are $R^2$ groups, and the other is an —O—Si— bond or an $R^2$ group; and "n" represents an integer of 0 to 10.

2. The silicon-containing compound having an alkoxysilyl-ethylene group at its terminal according to claim 1, which is selected from the group consisting of the following formulae:

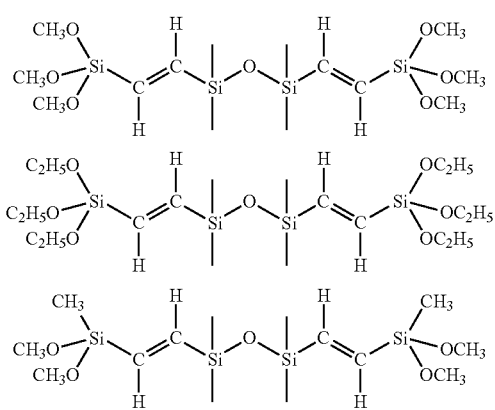

-continued

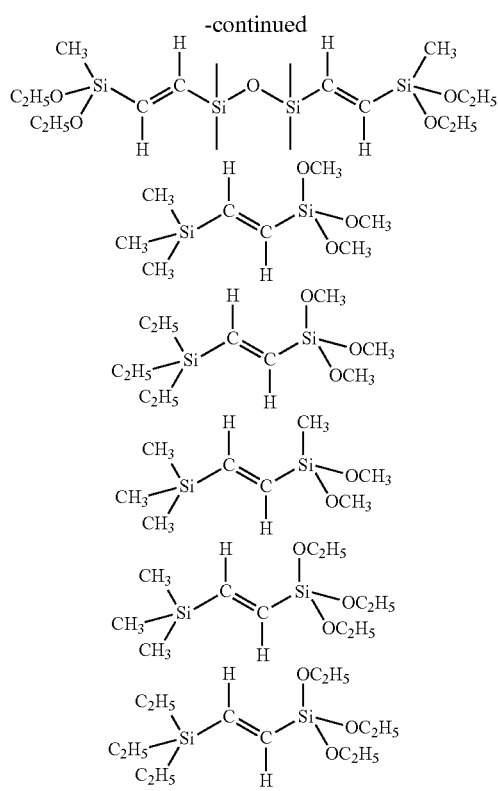

3. An organosiloxane compound having an alkoxysilyl-ethylene group at its terminal which comprises at least one silyl-ethylene bond represented by the following structural formula (1) in one molecule,

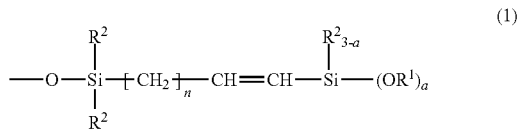

wherein $R^1$ represents a monovalent hydrocarbon group having 1 to 20 carbon atoms which may have a substituent, and those having 3 or more carbon atoms among the hydrocarbon groups may be a cycloalkyl group which is cyclic; $R^2$ represents a hydrogen atom, or a monovalent hydrocarbon group having 1 to 20 carbon atoms which may have a substituent; "a" represents an integer of 1 to 3; and "n" represents an integer of 0 to 10.

4. A silicon-containing compound having an alkoxysilyl-ethylene group at its terminal represented by the following structural formula (2),

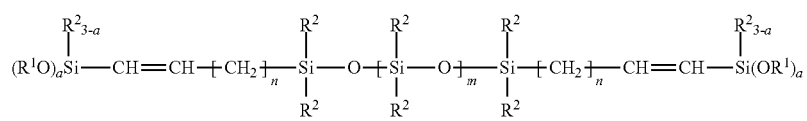 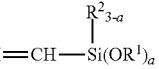

wherein $R^1$ represents a monovalent hydrocarbon group having 1 to 20 carbon atoms which may have a substituent, and those having 3 or more carbon atoms among the hydrocarbon groups may be a cycloalkyl group which is cyclic; $R^2$ represents a hydrogen atom, or a monovalent hydrocarbon group having 1 to 20 carbon atoms which may have a substituent; "a" represents an integer of 1 to 3; and "n" represents an integer of 0 to 10; and "m" represents an integer of 0 to 2,000.

5. The silicon-containing compound having an alkoxysilyl-ethylene group at its terminal according to claim 4, wherein "m" represents an integer of 0 to 500 in the structural formula (2).

6. The silicon-containing compound having an alkoxysilyl-ethylene group at its terminal according to claim 4, wherein the silicon-containing compound having an alkoxysilyl-ethylene group at its terminal is a disiloxane compound, where "m" represents 0 in the structural formula (2).

7. A room temperature-curable organopolysiloxane composition comprising:
  (A) a diorganopolysiloxane containing at least 2 silicon atoms to which a hydroxyl group and/or a hydrolyzable group are bonded in one molecule: 100 parts by mass;
  (B) the silicon-containing compound having an alkoxysilyl-ethylene group at its terminal according to claim 6; 0.1 to 30 parts by mass;
  (C) a curing catalyst: 0.001 to 15 parts by mass:
  (D) a silane and/or a partial hydrolysis condensate thereof other than the component (B): 0 to 30 parts by mass;
  (E) a filler: 0 to 1,000 parts by mass; and
  (F) an adhesion promoter: 0 to 30 parts by mass.

8. The silicon-containing compound having an alkoxysilyl-ethylene group at its terminal according to claim 4, wherein the silicon-containing compound having an alkoxysilyl-ethylene group at its terminal is a low-molecular-weight siloxane oligomer where "m" represents an integer of 1 to 10 in the structural formula (2).

9. A room temperature-curable organopolysiloxane composition comprising:
  (A) a diorganopolysiloxane containing at least 2 silicon atoms to which a hydroxyl group and/or a hydrolyzable group are bonded in one molecule: 100 parts by mass;
  (B) the silicon-containing compound having an alkoxysilyl-ethylene group at its terminal according to claim 8: 0.1 to 30 parts by mass;
  (C) a curing catalyst: 0.001 to 15 parts by mass;
  (D) a silane and/or a partial hydrolysis condensate thereof other than the component (B): 0 to 30 parts by mass;
  (E) a filler: 0 to 1,000 parts by mass; and
  (F) an adhesion promoter: 0 to 30 parts by mass.

10. A room temperature-curable organopolysiloxane composition comprising:
  (A) a diorganopolysiloxane containing at least 2 silicon atoms to which a hydroxyl group and/or a hydrolyzable group are bonded in one molecule: 100 parts by mass;
  (B) the silicon-containing compound having an alkoxysilyl-ethylene group at its terminal according to claims 7: 0.1 to 30 parts by mass;

(C) a curing catalyst: 0.001 to 15 parts by mass;
(D) a silane and/or a partial hydrolysis condensate thereof other than the component (B): 0 to 30 parts by mass;
(E) a filler: 0 to 1,000 parts by mass; and
(F) an adhesion promoter: 0 to 30 parts by mass.

11. A room temperature-curable organopolysiloxane composition comprising:
(A) a diorganopolysiloxane containing at least 2 silicon atoms to which a hydroxyl group and/or a hydrolyzable group are bonded in one molecule: 100 parts by mass;
(B) a silicon-containing compound having an alkoxysilyl-ethylene group at its terminal which comprises at least one silyl-ethylene bond represented by the following structural formula (a) in one molecule: 0.1 to 30 parts by mass;

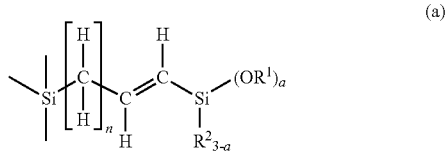

(a)

wherein $R^1$ represents a monovalent hydrocarbon group having 1 to 20 carbon atoms which may have a substituent, and those having 3 or more carbon atoms among the hydrocarbon groups may be a cycloalkyl group which is cyclic; $R^2$ represents a hydrogen atom, or a monovalent hydrocarbon group having 1 to 20 carbon atoms which may have a substituent; "a" represents an integer of 1 to 3; and "n" represents an integer of 0 to 10;
(C) a curing catalyst: 0.001 to 15 parts by mass;
(D) a silane and/or a partial hydrolysis condensate thereof other than the component (B): 0 to 30 parts by mass;
(E) a filler: 0 to 1,000 parts by mass; and
(F) an adhesion promoter: 0 to 30 parts by mass.

12. A coating agent, an adhesive or a sealing agent comprising the room temperature-curable organopolysiloxane composition according to claim 11.

13. A molded product obtained by curing the room temperature-curable organopolysiloxane composition according to claim 11.

14. A room temperature-curable organopolysiloxane composition comprising:
(A) a diorganopolysiloxane containing at least 2 silicon atoms to which a hydroxyl group and/or a hydrolyzable group are bonded in one molecule: 100 parts by mass;
(B) a silicon-containing compound having an alkoxysilyl-ethylene group at its terminal which comprises at least one silyl-ethylene bond represented by the following structural formula (1) in one molecule: 0.1 to 30 parts by mass;

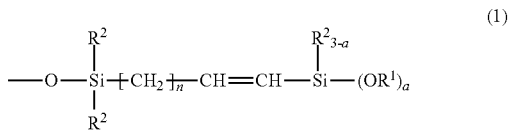

(1)

wherein $R^1$ represents a monovalent hydrocarbon group having 1 to 20 carbon atoms which may have a substituent, and those having 3 or more carbon atoms among the hydrocarbon groups may be a cycloalkyl group which is cyclic; $R^2$ represents a hydrogen atom, or a monovalent hydrocarbon group having 1 to 20 carbon atoms which may have a substituent; "a" represents an integer of 1 to 3; and "n" represents an integer of 0 to 10;
(C) a curing catalyst: 0.001 to 15 parts by mass;
(D) a silane and/or a partial hydrolysis condensate thereof other than the component (B): 0 to 30 parts by mass;
(E) a filler: 0 to 1,000 parts by mass; and
(F) an adhesion promoter: 0 to 30 parts by mass.

15. A coating agent, an adhesive or a sealing agent comprising the room temperature-curable organopolysiloxane composition according to claim 14.

16. A molded product obtained by curing the room temperature-curable organopolysiloxane composition according to claim 14.

17. A room temperature-curable organopolysiloxane composition comprising:
(A) a diorganopolysiloxane containing at least 2 silicon atoms to which a hydroxyl group and/or a hydrolyzable group are bonded in one molecule: 100 parts by mass;
(B) the silicon-containing compound having an alkoxysilyl-ethylene group at its terminal according to claims 3: 0.1 to 30 parts by mass;
(C) a curing catalyst: 0.001 to 15 parts by mass;
(D) a silane and/or a partial hydrolysis condensate thereof other than the component (B): 0 to 30 parts by mass;
(E) a filler: 0 to 1,000 parts by mass; and
(F) an adhesion promoter: 0 to 30 parts by mass.

18. A coating agent, an adhesive or a sealing agent comprising the room temperature-curable organopolysiloxane composition according to claim 17.

19. A molded product obtained by curing the room temperature-curable organopolysiloxane composition according to claim 17.

* * * * *